United States Patent
Hall et al.

(10) Patent No.: US 9,827,394 B2
(45) Date of Patent: Nov. 28, 2017

(54) DISPERSION ANAESTHETIC DEVICE

(71) Applicant: University College Cardiff Consultants Limited, Cardiff (GB)

(72) Inventors: Judith Hall, Cardiff (GB); Alison Paul, Caerphilly (GB); Antony Wilkes, Hengoed (GB)

(73) Assignee: University College Cardiff Consultants Limited, Cardiff (GB)

( * ) Notice: Subject to any disclaimer, the term of this patent is extended or adjusted under 35 U.S.C. 154(b) by 747 days.

(21) Appl. No.: 14/344,126

(22) PCT Filed: Sep. 18, 2012

(86) PCT No.: PCT/GB2012/052302
§ 371 (c)(1),
(2) Date: Mar. 11, 2014

(87) PCT Pub. No.: WO2013/041850
PCT Pub. Date: Mar. 28, 2013

(65) Prior Publication Data
US 2014/0216456 A1    Aug. 7, 2014

(30) Foreign Application Priority Data
Sep. 21, 2011 (GB) .................................. 1116271.6

(51) Int. Cl.
*A61M 16/18* (2006.01)
*A61M 16/10* (2006.01)
(Continued)

(52) U.S. Cl.
CPC ............... *A61M 16/18* (2013.01); *A61D 7/04* (2013.01); *A61K 9/0073* (2013.01);
(Continued)

(58) Field of Classification Search
CPC ...... A61M 16/00; A61M 16/06; A61M 16/10; A61M 16/104; A61M 16/14; A61M 16/18;
(Continued)

(56) References Cited

U.S. PATENT DOCUMENTS 2,046,633 A    7/1936  Johnson
2,246,964 A    6/1941  Wolfe
(Continued)

FOREIGN PATENT DOCUMENTS

GB    630481 A    10/1949
GB    1454795 A    11/1976
(Continued)

OTHER PUBLICATIONS

International Search Report and Written Opinion for International application No. PCT/GB2012/052302 dated Jul. 16, 2013.
(Continued)

*Primary Examiner* — Justine Yu
*Assistant Examiner* — Colin W Stuart
(74) *Attorney, Agent, or Firm* — King & Schickli, PLLC

(57) ABSTRACT

The invention concerns a cartridge for an inhalation device for delivering anaesthetic to a human or animal wherein anaesthetic in the cartridge is dispersed in an anaesthetic control release medium; an inhalation device for use with the cartridge and a formulation including at least one selected anaesthetic and anaesthetic control release medium.

13 Claims, 32 Drawing Sheets

(51) Int. Cl.
*A61M 16/14* (2006.01)
*A61K 9/00* (2006.01)
*A61K 9/107* (2006.01)
*A61M 15/00* (2006.01)
*A61D 7/04* (2006.01)

(52) U.S. Cl.
CPC ....... *A61K 9/1075* (2013.01); *A61M 15/0006* (2014.02); *A61M 16/10* (2013.01); *A61M 16/104* (2013.01); *A61M 16/14* (2013.01); *A61M 2016/1035* (2013.01); *A61M 2202/048* (2013.01); *A61M 2205/123* (2013.01); *A61M 2209/06* (2013.01)

(58) Field of Classification Search
CPC ............ A61M 16/009; A61M 16/0093; A61M 19/00; A61M 15/005; A61M 15/006; A61D 7/04; A61K 9/1075
See application file for complete search history.

(56) References Cited

U.S. PATENT DOCUMENTS

| | | | |
|---|---|---|---|
| 2,549,593 A | | 4/1951 | Gardenier |
| 3,018,777 A | | 1/1962 | Dietrich |
| 4,148,312 A | | 4/1979 | Bird |
| 5,231,980 A | * | 8/1993 | Filipovic ............ A61M 16/0087 128/205.12 |
| 6,451,335 B1 | * | 9/2002 | Goldenheim ........ A61K 9/1647 424/426 |
| 2003/0140921 A1 | * | 7/2003 | Smith ..................... A61J 1/065 128/200.14 |
| 2004/0082651 A1 | * | 4/2004 | Wessjohann .......... C07F 7/1856 514/475 |
| 2005/0032912 A1 | * | 2/2005 | Garrett ................. A61K 9/0073 514/731 |
| 2006/0198891 A1 | * | 9/2006 | Ravenelle ............ A61K 9/0019 424/486 |
| 2008/0020044 A1 | * | 1/2008 | Alam ................... A61K 9/0048 424/486 |
| 2008/0234389 A1 | * | 9/2008 | Mecozzi ............. A61K 9/0019 514/722 |
| 2011/0073108 A1 | | 3/2011 | Bird |
| 2011/0159078 A1 | * | 6/2011 | Burton ................ A61K 9/0014 424/450 |
| 2011/0306676 A1 | * | 12/2011 | Dunlop ................... A61D 7/04 514/722 |

FOREIGN PATENT DOCUMENTS

| | | |
|---|---|---|
| GB | 1555982 A | 11/1979 |
| GB | 2350297 A | 11/2000 |
| WO | 9417819 A1 | 8/1994 |
| WO | 9629052 A1 | 9/1996 |
| WO | 9955286 A2 | 11/1999 |
| WO | 9958555 A2 | 11/1999 |
| WO | 03030862 A2 | 4/2003 |
| WO | 2008070490 A2 | 6/2008 |
| WO | 2009094460 A2 | 7/2009 |
| WO | 2011061332 A1 | 5/2011 |
| WO | 2013016511 A1 | 1/2013 |

OTHER PUBLICATIONS

Jonathon P. Fast, et al.; "Fluoropolymer-Based Emulsions for the Intravenous Delivery of Sevoflurane"; Anesthesiology, vol. 109, No. 4, pp. 651-656; Oct. 2008.

Search Report for British Application No. GB1021512.7 dated Feb. 23, 2011.

Search Report for British Application No. GB1116271.6 dated Jan. 12, 2012.

* cited by examiner $C_8F_{17}C_2H_4SO_2NH[CH_2CH(CH_2OH)O]_nH$ (h)

$R_fCH_2CH(OH)CH_2NH(CH_2)_3O[(CH_2)_4O]_8(CH_2)_3NHCH_2CO$ (i)

$C_8F_{17}SO_2NH(CH_2)_3NH(CH_2)_3NHCH_2CH_2OSO_3Na$ (j)

$CF_3C(CF_2)_7SO_2N(C_2H_5)CH_2CH_2OP(O)(ONa)_2$ (k)

$R_fCH_2CH_2SCH_2CH(OSO_3)CH_2N(CH_3)_3$

Figure 4 continued (A) fluorocarbon – ethylene oxide;

(b) propylene oxide – ethylene oxide;

(c) larger ethylene oxides with methoxy end-group functionality;

(d) polyoxyethylene derivative of sorbitan monolaurate;

(e) fluorinated polyhydric alcohols;

(f) ethoxylated fatty alcohols ;

(g) partially fluorinated sulfosuccinates; highly branched hydrocarbon sulfosuccinates;

(h) propylene oxide – fluorocarbon–ethylene oxide surfactant ;

(i) perfluoroalkylated aminocarboxylates with oxy and hydroxy groups;

(j) fluorinated aminosulfate;

(k) perfluoroalkanesulfonamide derivatives ;

(l) fluorinated sulfobetaines;

(m) perfluoroalkanesulfonamido group;

(n) perfluoroalkylethyl phosphates ;

(o) perfluoroalkyl phosphates ;

(p) perfluoroalkyl-2-ethanethiol derivatives ;

(q) silicon-containing fluorinated surfactants;

(r) perfluoroalkylsulfopropionates and sulfobutyrate;

(s) polyfluroinated ketones;

(t) perfluoroalkanoic acid;

(u) fluorinated alkanoic acid;

(v) perfluoropolyether carboxylic acids;

(w) perfluoroalkyl salts;

(x) perfluoroalkanesulfonic acids or salts;

(y) perfluoropropoxylated sulphate;

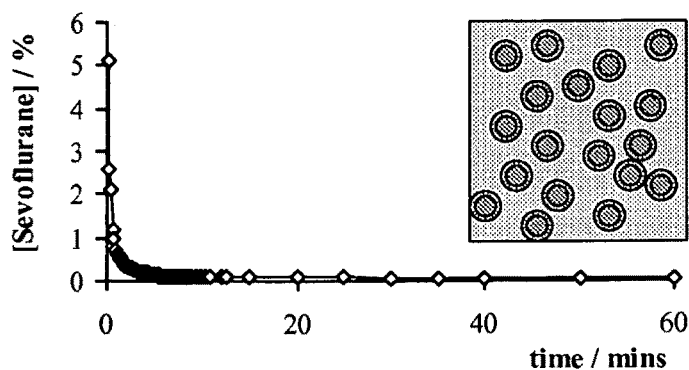
Figure 5
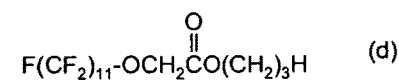
(d)
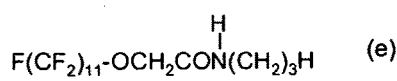
(e)
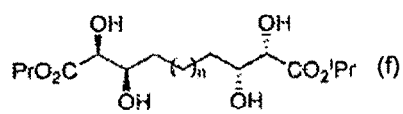
(f)
4 a) n = 3   c) n = 5
  b) n = 4   d) n = 6
             e) n = 8
Figure 6

Figure 42 a & b

DISPERSION ANAESTHETIC DEVICE

This application is the national stage of international patent application no. PCT/GB2012/052302 filed on Sep. 18, 2012, which in turn claims priority from British Patent Application Ser. No. 1116271.6 filed on Sep. 21, 2011, the disclosures of which are incorporated herein by reference in their entirety.

TECHNICAL FIELD OF THE INVENTION

The invention relates to a novel anaesthetic cartridge for use with an inhalation device; a method of delivering volatilised anaesthetic using the cartridge of the invention in combination with an inhalation device; an inhalation device comprising the afore mentioned cartridge; formulations comprising an anaesthetic control release medium and at least one anaesthetic for use in the cartridge of the invention.

BACKGROUND OF THE INVENTION

Ethically, the delivery of combined anaesthesia and analgesia is mandatory for surgical procedures in even the most difficult situations, or underdeveloped countries of the world. In order to facilitate surgery, approximately 27 million anaesthetics are given each year in the USA and 8 million are given each year in the UK. A worldwide estimate of activity suggests that over 200 million anaesthetics are given each year globally. Volatile anaesthetic agents can not only provide full anaesthesia, but also sedation and some degree of analgesia. Other drugs for sedation and analgesia are often co-administered.

Simplification of the anaesthetic process would be of great benefit, in terms of both patient safety and expense to healthcare systems. Moreover, a simple and effective way to administer anaesthesia would mean that pre-hospital care or ambulatory medicine could include important procedures that a patient presently may find too uncomfortable to tolerate outside of an operating theatre. Additionally, it could also facilitate sedation of a badly injured person whilst they were transported, in some instances over hostile terrain, to a healthcare facility.

With this in mind we have developed a novel solution for the delivery of anaesthetic agents. The system that we have developed is:
a. simple,
b. inexpensive,
c. less labour intensive (as less checking is required);
d. safe for patients, with less things to go wrong.

In particular we have devised a system that is compatible with human or veterinary use, is of low volume (thus reducing bulk to enable safe anaesthesia), is physically stable during storage, functions rapidly and the anaesthetic is completely volatilized for patient safety.

BRIEF SUMMARY OF THE INVENTION

According to a first aspect of the invention there is provided an anaesthetic cartridge for use with an inhalation device to deliver an inhalational or volatilised anaesthetic to a patient wherein said cartridge comprises or consists of: an adjustable stirrer or agitator; an anaesthetic control release medium and at least one selected inhalation anaesthetic, wherein the amount of said medium relative to said anaesthetic is such that when using said adjustable stirrer or agitator anaesthetic is delivered at a selected Minimum alveolar concentration (MAC), at a substantially constant or controllable rate, within the range of 0.125-4.0× Minimum alveolar concentration (MAC) thereby allowing for either i) induction and/or maintenance of anaesthesia or ii) sedation.

In a preferred embodiment of the invention adjustment of said stirrer or agitator enables a user to select any MAC value within said range, including but not limited to all 0.05 MAC intervals. Typically increased stirring or agitation increases, the amount of anaesthetic released and so the effective MAC value, whereas decreased stirring or agitation decreases the amount of anaesthetic released and so decreases the effective MAC value. Preferably said MAC value is selected from the group comprising: 0.125, 0.25, 0.35, 0.5, 0.65, 0.7, 1.0, 1.33, 1.5, 1.70, 1.75, 2.0, 2.5, 3.0, 3.5 and 4.0× Minimum alveolar concentration (MAC).

According to a second aspect of the invention there is provided an anaesthetic cartridge for use with an inhalation device to deliver an inhalational or volatilised anaesthetic to a patient wherein said cartridge comprises or consists of: a stirrer or agitator; an anaesthetic control release medium and at least one selected inhalation anaesthetic and further wherein the amount of said medium relative to said anaesthetic is such that when using said cartridge in an inhalation device and so using the stirrer or agitator at a selected rate anaesthetic is delivered at a substantially constant or controllable rate within the range of 0.125-4.0× Minimum alveolar concentration (MAC) thereby allowing for either i) induction of anaesthesia or ii) maintenance of anaesthesia or iii) sedation.

In a preferred embodiment of the invention the amount of said medium relative to said anaesthetic is such that when using said cartridge in an inhalation device anaesthetic is delivered at a substantially constant or controllable rate within said range, including but not limited to all 0.05 MAC intervals. Preferably said MAC value is selected from the group comprising: 0.125, 0.25, 0.35, 0.5, 0.65, 0.7, 1.0, 1.33, 1.5, 1.70, 1.75, 2.0, 2.5, 3.0, 3.5 and 4.0× Minimum alveolar concentration (MAC).

In a further preferred embodiment of the invention said stirrer or agitator is adjustable whereby the shearing force generated thereby is adjustable.

Minimum alveolar concentration (MAC) referred to herein is the concentration of vapour (measured as a percentage at 1 atmosphere, i.e. the partial pressure) that prevents the reaction to a standard surgical stimulus (traditionally a skin incision by a surgical knife) in 50% of subjects. This measurement is done at steady state (assuming a constant alveolar concentration for 15 minutes), under the assumption that this allows for an equilibration between the gasses in the alveoli, the blood and the brain. MAC is accepted as a valid measure of potency of inhalational general anaesthetics because it remains fairly constant for a given species even under varying conditions. The MAC values referred to herein are for an average adult male at age 40 years.

MAC values vary for different volatile agents. A MAC value of 1 for sevoflurane is (release level) 2 volume %, a MAC value of 1 for isoflurane is 1.2 volume %, a MAC value of 1 for halothane is 0.76 volume %, a MAC value of 1 for enflurane is 1.6 volume % and a MAC value of 1 for desflurane is 6 volume %.

Accordingly, in an anaesthetic cartridge of the invention having a MAC value of 1 the amount of said anaesthetic control release medium is such that said anaesthetic is released at 2 volume % for sevoflurane, 1.2 volume %, for isoflurane, 0.76 volume % for halothane, 1.6 volume % for enflurane and 6 volume % for desflurane.

In the instance of sevoflurane, this can be achieved in a system having a flow rate of 1 L/min per 120 ml formulation using e.g. 15 ml of sevoflurane and 105 ml of said anaesthetic control release medium containing 7 wt % of surfactant, preferably Zonyl FSN-100. In the instance of isoflurane, this can be achieved in a system having a flow rate of 1 L/min per 110 ml formulation using e.g. 12 ml of isoflurane and 98 ml of said anaesthetic control release medium containing 12 wt % of surfactant, preferably Zonyl FSN-100; or, using e.g. per 100 ml formulation using 9 ml of isoflurane and 91 ml of said anaesthetic control release medium containing 1 wt % of surfactant, preferably Zonyl FSN-100.

Those skilled in the art will appreciate that the invention can be worked using formulation volumes of 120 ml, 110 ml or 100 ml as afore described or corresponding milliliter multiples and/or fractions thereof, or indeed, any of the formulation volumes described herein including the corresponding milliliter multiples and/or fractions thereof.

In a further preferred embodiment of the invention, said anaesthetic cartridge delivers anaesthetic at a substantially constant or controllable rate of 1.0× Minimum alveolar concentration (MAC), and so has a MAC value of 1, and comprises, or consists of, any of the formulations herein described with said MAC value of 1 or any of the other formulations which are stirred, agitated or sheared to have a MAC value of 1.

In alternative embodiments of the invention said anaesthetic cartridge delivers at a substantially constant rate of 0.125, 0.25, 0.35, 0.5, 0.65, 0.7, 1.0, 1.33, 1.5, 1.70, 1.75, 2.0, 2.5, 3.0, 3.5 and 4.0× Minimum alveolar concentration (MAC) and so has a MAC value of 0.125, 0.25, 0.35, 0.5, 0.65, 0.7, 1.0, 1.33, 1.5, 1.70, 1.75, 2.0, 2.5, 3.0, 3.5 and 4.0, respectively, and comprises, or consists of, any of the formulations herein described with said corresponding MAC value or any of the other formulations which are stirred, agitated or sheared to have said corresponding MAC value.

In an anaesthetic cartridge of the invention having a MAC value of 2 the amount of said anaesthetic control release medium is such that said anaesthetic is released at 4 volume % for sevoflurane, 2.4 volume %, for isoflurane, 1.52 volume % for halothane, 3.2 volume % for enflurane and 12 volume % for desflurane.

For example, in the instance of sevoflurane, this can be achieved in a system having a flow rate of 1 L/min per 160 ml formulation using e.g. 50 ml of sevoflurane and 110 ml of said anaesthetic control release medium containing 18 wt % of surfactant, preferably Zonyl FSN-100. For example, in the instance of isoflurane, this can be achieved in a system having a flow rate of 1 L/min per 100 ml formulation using e.g. 15 ml of isoflurane and 85 ml of said anaesthetic control release medium containing 22 wt % of surfactant, preferably Zonyl FSN-100.

MAC values up to and including 4 MAC may be obtained. For example, as shown in FIG. 47, in a system having a flow rate of 1 L/min in the instance of sevoflurane, 3MAC and 4MAC can be achieved per 160 ml formulation using e.g. 50 ml of sevoflurane and 110 ml of said anaesthetic control release medium containing 15 wt % of surfactant, preferably Zonyl FSN-100. Further, for example, as shown in FIG. 48, in a system having a flow rate of 1 L/min in the instance of isoflurane, 4MAC can be achieved per 120 ml formulation using e.g. 20 ml of isoflurane and 100 ml of said anaesthetic control release medium containing 16 wt % of surfactant, preferably Zonyl FSN-100.

Alternatively, in a system having a flow rate of 4 L/min, 2MAC can be achieved for sevoflurane using a formulation consisting of 70 ml Sevoflurane and 90 ml of said anaesthetic control release medium containing 25 wt % surfactant, preferably Zonyl FSN-100, as shown in Table 8 and FIG. 49a or, also in a system having a flow rate of 4 L/min this can be achieved for isoflurane using a formulation consisting of 30 ml isoflurane and 100 ml of said anaesthetic control release medium containing 23 wt % surfactant, preferably Zonyl FSN-100 as shown in Table 9 and FIG. 49*b*.

For sedation purposes lower MAC values are sufficient. For example, in a system having a flow rate of 1 L/min for sevoflurane sustained release at 0.25 MAC can be achieved per 90 ml formulation using e.g. 5.5 ml of sevoflurane and 84.5 ml of said anaesthetic control release medium containing 8 wt % of surfactant, preferably Zonyl FSN-100, as shown in table 5. For example, in a system having a flow rate of 1 L/min in the instance of isoflurane this can be achieved per 80 ml formulation using e.g. 2.5 ml of isoflurane and 77.5 ml of said anaesthetic control release medium containing 13 wt % of surfactant, preferably Zonyl FSN-100, as shown in table 5.

For example, in a system having a flow rate of 1 L/min for sevoflurane sustained release at 0.5 MAC can be achieved per 120 ml formulation using e.g. 7.5 ml of sevoflurane and 112.5 ml of said anaesthetic control release medium containing 4 wt % of surfactant, preferably Zonyl FSN-100 as shown in table 5. For example, in a system having a flow rate of 1 L/min in the instance of isoflurane this can be achieved per 100 ml formulation using e.g. 4.5 ml of isoflurane and 95.5 ml of said anaesthetic control release medium containing 8 wt % of surfactant, preferably Zonyl FSN-100, as shown in table 5.

Those skilled in the art will appreciate that the invention can be worked using formulation volumes as afore described or corresponding milliliter multiples and/or fractions thereof or, indeed, any of the formulation volumes described herein including the corresponding milliliter multiples and/or fractions thereof.

Reference herein to a substantially constant or controllable rate is reference to release of volatilised anaesthetic at a given MAC value or vol % to within 0.2% of drift or to adjustment of release of volatilised anaesthetic to an alternative MAC value or vol % again within 0.2% of drift, respectively.

The selection of a cartridge providing a given MAC value can vary according to the physiological status of the patient, their age and the co-administration of other drugs or medicines. At low concentrations of anaesthetic, or low MAC values, the risk is that insufficient anaesthetic is delivered to the patient to maintain anaesthesia. At high concentrations, volatile anaesthetic agents have a depressant effect on the respiratory and cardiovascular system. Physiological parameters are therefore carefully monitored during anaesthesia to judge that the correct dose is administered. Typically, to maintain anaesthesia, an adult is likely to receive 1×MAC, whereas a child may receive up to 2×MAC of the equivalent of an adult. However, cartridges with MAC values less than 1 may be used for the purpose of sedation. Thus, in use, a cartridge is selected having regard to the most appropriate MAC value for the patient and use in question. However, to ensure some flexibility of administration the cartridge, in a first aspect of the invention, is provided with an adjustable stirrer or agitator and, in the second aspect of the invention, is, ideally, further provided with an adjustable stirrer or agitator whereby the amount of stirring or agitating of the anaesthetic control release medium and the anaesthetic can be varied, thus influencing the release level of the anaesthetic and so, temporarily, or for a time period equal to the adjusted level of stirring or agitating, said MAC value can be raised or lowered.

In the examples disclosed herein the cartridge of the invention includes an adjustable stirrer which is a conventional bar magnet stirrer 6 cm×1 cm.

For example, when using sevoflurane: for each 120 ml formulation of 15 ml of sevoflurane and 105 ml of said anaesthetic control release medium containing 7 wt % of surfactant, a stirring rate of 250 rpm will release anaesthetic at a 1 MAC value, but if the stirring is increased to 500 rpm the MAC value increases to 1.7 MAC. Also, decreasing the stirring rate to 100 rpm gives 0.35 MAC (0.7 vol %). Please see FIG. 37. As an alternative example, shown in FIG. 47, using a 160 ml formulation of 50 mL sevoflurane and 110 mL of aqueous solutions of 15 wt. % Zonyl FSN-100, stirring rates between 500-50 rpm, as shown in Table 10, result in release of anaesthetic at a value of between 4.0-0.125 MAC under Nitrogen flow rate of 1 L min$^{-1}$ as a function of stirring speed using Flow-Rig Model 6 (S.A.=50 cm$^2$).

In another example, in the instance of isoflurane: for each 120 ml formulation using 20 ml of isoflurane and 100 ml of said anaesthetic control release medium containing 16 wt % of surfactant a stirring rate of 200 rpm will release anaesthetic at a 0.5 MAC value, but if the stirring is increased to 315 rpm or more, i.e. up to 375 rpm the MAC value increases to 4 MAC, as shown in table 11.

In one embodiment of the invention said adjustable stirrer is made to operate between 50-1000 rpm including all 1 rpm increments in between, and, ideally, between 200-500 rpm including all 1 rpm increments in between. In this embodiment of the invention said stirrer is a conventional bar magnet stirrer 6 cm×1 cm. However those skilled in the art will appreciate that other forms of stirrers, or agitators may be used such as, without limitation, a paddle stirrer, a propeller etc., of different sizes, blade pitch, surface area etc. or an agitator such as a vibrational agitator. Each stirrer or agitator, depending upon the shear forces created, would be used at different stirring or agitation rates for a given volume % release of anaesthetic or MAC value. However the determination of this stirring or agitation rates by each stirrer or agitator would be understood and achievable by those skilled in the art. Thus, in use, each cartridge is calibrated having regard to the shearing device to be used therein so that the invention described herein, including all the formulations given as examples, releases a certain amount of volatilised anaesthetic when stirred or agitated using a given stirrer or agitator at a given rate.

When using only an inhalational anaesthetic to induce and maintain anaesthesia, it is common practice to start with up to 4 times MAC, which is generally administered until loss of consciousness, and then to reduce the concentration of the inhalational anaesthetic to 0.25-2.0 MAC with a view to maintaining anaesthesia, but this is dependent on the physiological response of the patient. As mentioned above, to maintain anaesthesia a child is likely to require a higher concentration of anaesthetic than an adult who is likely to need 1×MAC to maintain anaesthesia, whereas a child is likely to need 2×MAC of the equivalent of an adult to maintain anaesthesia.

Thus the invention can be used in such a way that stirring or agitation is set to provide for administration of anaesthetic at 4 MAC until unconsciousness is achieved and then the stirring or agitation can be adjusted to ensure a selected lower MAC, such as 1×MAC for and an adult and 2×MAC of the equivalent of an adult for a child to maintain anaesthesia. As is also mentioned above, the anaesthetic release cartridge is calibrated having regard to the type of stirrer or agitator used and, typically, instructions are provided concerning the required stirring or agitating of cartridge contents for each MAC value.

As an alternative, an intravenous injection of anaesthetic may be used to achieve unconsciousness and so, when using both an intravenous anaesthetic and an inhalation anaesthetic, after intravenous induction of unconsciousness, an initial 4×MAC concentration of the inhalational agent is generally not required, so adjustment of a stirring device in a given MAC cartridge is typically not required to maintain unconsciousness.

Those skilled in the art will appreciate that the total volume of anaesthetic agent required for each patient will also depend on the flow of gas (oxygen, air or nitrous oxide) into the cartridge/inhalation device and delivered to the patient (as well as the anaesthetic requirements of the patient). Typically a flow rate of 1 L/min is used. Flow rates depend on the type of anaesthetic breathing system used to deliver the gases to the patient, with the design of the breathing system dictating efficiency of the removal of the patient's exhaled carbon dioxide gas. Typical flow rates might be 1 L min$^{-1}$ for a circle breathing system and 3-5 L min$^{-1}$ for a Mapleson A breathing system. The cartridges of the invention are therefore calibrated with this in mind.

As surgical procedures continue for varying lengths of time the invention encompasses different volume cartridges. Thus, in the above referred to formulations, those skilled in the art will appreciate that the invention can be worked using formulation volumes as herein described or corresponding milliliter multiples and/or fractions thereof. Additionally, or alternatively, the invention comprises the use of multiple cartridges per MAC value of a standard size where each additional cartridge used is referred to as a "plug in" extra cartridge.

In one, embodiment of the invention we have calculated that the required volume of selected inhalation anaesthetic for an adult e.g. sevoflurane is about 12.5 ml to maintain 2% for one hour, which at a formulation content of between 5 and 50% by volume gives us approximately 25-150 ml of anaesthetic control release medium per hour.

In a preferred embodiment of the invention the amount of said medium relative to said anaesthetic is such that when using said inhalation device a large dose of said anaesthetic is delivered within a first short interval to achieve a requisite Minimum Alveolar Concentration (MAC) of 1-4×MAC for the said anaesthetic and the remaining amount of anaesthetic is delivered at a substantially constant or controllable rate of 0.25-2.0×MAC over a second long interval thereby allowing for initial overpressure of the anaesthetic during the induction of anaesthesia, followed by an anaesthesia maintenance phase. Please see FIGS. 9-16, and 18-20.

Overpressure of anaesthesia is desirable to anaethetise a patient and is the accepted term for the administration of an amount of anaesthesia sufficient to achieve this effect via an over-concentration of anaesthetic gas or vapour.

In yet a further preferred embodiment, where unconsciousness is to be instigated and then maintained using only the invention, i.e. without an intravenous anaesthetic, the anaesthetic is ideally delivered in a manner similar to the delivery profile shown in FIG. 5, using the adjustable stirrer or agitator, where up to 80%, preferably up to 40%, typically up to 10% and most typically 5-10% of the total amount of anaesthetic is delivered in the first 30 seconds to 5 minutes and the remainder is delivered, after a slowing down period, at a relatively constant rate for a period of up to one hour. Thus the cartridge provides sufficient anaesthetic for surgery or sedation lasting up to one hour to take place. Typically, operating instructions for the use of the stirrer or agitator, and so the varying of the MAC values, are provided with each cartridge. Please see FIGS. 5, 20, and 34.

As mentioned, MAC also varies with age, so that the concentration of anaesthetic required to maintain anaesthesia in young patients is more than for older patients. Thus, in further embodiments of the invention said cartridge is available in at least three formulations for the purpose of maintaining anaesthesia: a first formulation where the combination of anaesthetic control release medium and anaesthetic is appropriate for paediatric use: 2.0 MAC of the equivalent of an adult; a second formulation where the combination of anaesthetic control release medium and anaesthetic is appropriate for adult use: 1.0 MAC; and a third formulation where the combination of anaesthetic control release medium and anaesthetic is appropriate for geriatric use: 0.5 MAC of the equivalent of an adult. In each instance the total amount of anaesthetic in the formulation, or cartridge, for delivery to a patient is an amount to maintain constant anaesthesia for 60 min.

Accordingly, in a further aspect the invention comprises a kit comprising a plurality of anaesthetic cartridges as herein described wherein said cartridges are either of the same or different MAC values.

The invention therefore also provides for different cartridges, both in terms of size and/or content, for different types of patient and for different lengths of operation, moreover, the invention includes additional plug-in cartridges for extended use times. Any of these different cartridges may be included in the kit of the invention. Additionally, said kit ideally includes a set of instructions concerning the use of selected, and ideally, each cartridge which preferably indicates the effective amount of time each cartridge can be used at a selected stirring or agitation rate and/or flow rate and ideally also at a set temperature, although in most instances a standard will be used and in a circle system we suggest this standard will be a time of 1 hour per cartridge at a stirring rate of 250 rpm (using a 6 cm×1 cm bar magnet or an equivalent shearing force provided by an alternative stirrer or agitator) and a flow rate at 1 L/min at a temperature of 20° C., or in a Mapleson A system we suggest this standard will be a time of 1 hour per cartridge at a stirring rate of 350 rpm (using a 6 cm×1 cm bar magnet or an equivalent shearing force provided by an alternative stirrer or agitator) and a flow rate at 1 L/min at a temperature of 20° C.

As those skilled in the art will appreciate the release of anaesthetic from said cartridge, when used in a conventional fashion, will be controlled, to some extent, by the rate of flow of breathable gas over or through the anaesthetic control release medium. However, the invention is intended for use at what is typically considered to be a reasonable or normal flow rate of 1 liter of breathable gas/minute into the device, although the device will function from 0.5-15 L of fresh gas flow/minute.

In circumstances where a sudden decrease in anaesthesia is desired this can be achieved by reducing the stirring, shaking or agitation of the cartridge, or indeed by any other method such as an increase in flow rate, and this will result in a sudden relative reduction in anaesthesia as depicted in FIG. 35. Skilled artisans will appreciate this action will alter the maximum length of time over which the cartridge can be used.

In a further preferred embodiment of the invention the anaesthetic is dispersed or distributed in said medium in a stable and chemically unaltered state.

In a further preferred embodiment of the invention said anaesthetic control release medium is a gel or an emulsion.

Emulsions enable hydrophobic molecules to be stably dispersed within water. In our invention we have created emulsions to disperse anaesthetic molecules in water. We have therefore used commercially available non-ionic surfactants including halogenated non-ionic surfactants such as an ethylene oxide based surfactant with a linear fluorocarbon hydrophobic chain, and a propylene oxide or a ethylene oxide hydrocarbon surfactant. Those skilled in the art will be aware of other known surfactants or stabilisers (including but not limited to polymers, particles, surfactants or lipids) that can be used to work the invention, as show in FIG. 4. Ideal surfactants are those with non-volatile properties whereby only the anaesthetic is released from the said anaesthetic control release medium when breathable gas passes therethrough or thereover. Using this embodiment an anaesthetic content of between 0.25-44%, i.e. 3.1-43.8% by volume (tables 5-9) can be achieved.

In a further preferred embodiment of the invention the emulsions may be nanoemulsions, microemulsions or macroemulsions.

In a further preferred embodiment of the invention the emulsions containing the surfactants and the at least one anaesthetic have a droplet size in the nm range and, ideally, between 10-1000 nm and most ideally between 50-1000 nm, preferably in the hundred nm range i.e. between 100-900 nm ideally, 118-884 nm including all the values shown in tables 5-9.

Reference herein to a surfactant includes reference to any surface-active agent that stabilizes mixtures of oil and water by adsorbing to and/or reducing the surface tension at the interface between the oil and water molecules.

More preferably the surfactant is one or more of Zonyl FSN-100, Capstone FS-63, Capstone FS-3100, Chemguard S-550L-100, Polyfox 159, Brij O20, and Tween including any and all combinations thereof.

More preferably still the surfactant is one or more of, including any and all combinations thereof, Zonyl FSN-100, Capstone FS-63, Capstone FS-3100, Chemguard S-550L-100, Polyfox 159, Polyfox 656, Polyfox 6520, Polyfox 636, Brij O20, Brij O5, Brij O10, Brij S2, Brij S721, Brij 35, Brij C2, Flexiwet NI-55, Novec FC 4430, Tween 60, Tween 80, Tween 20, Pluronics, BYK 340, Schwego Fluor EL 3711, Schwego Fluor EL 4311, WorleeAdd 386 F, WorleeAdd 380 F, Capstone FS-31, Capstone FS-65, Capstone FS-35, Novec 4200, Novec 4434, Dynol 607, Certonal 752 and Certonal 742 including any and all combinations thereof.

We have discovered that the slow diffusion of the anaesthetic through the emulsion to the surface affects the release thereof and so introduces an element of control into the system which can be fine tuned by appropriate stirring or controlled agitation.

Moreover, we have also discovered that for the purpose of transport the anaesthesia may be provided as a gel. Typical gelling agents for this are based on chiral, non-racemic bis-($\alpha,\beta$-dihydroxy ester)s. These are known to gel fluorocarbon liquids, including the model anaesthetic HPFP. Those skilled in the art wine aware of other known gelling agents that can be used to work this embodiment of the invention such as those shown in FIG. 6. Upon use, the selected surfactant solution i.e. the appropriate weight % and volume is added to the gel to dissolve the gel and so release said anaesthetic as a dispersion within the solution. Therefore, in yet a further alternative embodiment of the invention said anaesthetic control release medium and said at least one selected inhalation anaesthetic comprises an emulsion thickened with or comprising a gelling agent. In this embodiment of the invention, gelling the anaesthetic prior to reconstitution into liquified form using a surfactant does not affect the function of the formulation in terms of the controlled release of anaesthetic at a selected MAC value.

Accordingly, in yet an alternative aspect of the invention there is provided an anaesthetic cartridge for use with an inhalation device to deliver an inhalational or volatilised anaesthetic to a patient wherein said cartridge comprises or consists of: an adjustable stirrer or agitator, an anaesthetic control release medium, a gelling agent and at least one selected inhalation anaesthetic, wherein the amount of said medium and/or gelling agent relative to said anaesthetic is such that when using said adjustable stirrer or agitator anaesthetic is delivered at a selected Minimum Alveolar Concentration (MAC), at a substantially constant or controllable rate, within the range of 0.125-4.0× Minimum alveolar concentration (MAC) thereby allowing for either i) induction and/or maintenance of anaesthesia or ii) sedation.

Most gelators would be below 10 wt % gelator, but other gelators could be used at higher concentrations. Those skilled in the art will be aware of other known gelling agents that can be used to work the invention. In this embodiment of the invention the anaesthetic is safely stored in the gel until the point of use at which time water and/or surfactant may be added to solubilise and/or disperse the gel, typically assisted by shaking, to create a fluid, having a formulation as herein described, over which or through which a breathable gas can flow to entrain anaesthetic gas for the purpose of delivery to a patient. An example of a gelation mixture comprises or consists of 1 weight % gelator (such as 0.15 g of G4 in 15 ml Sevoflurane). Ideally, this would be reconstituted using 105 ml of 7 wt % Zonyl FSN-100. The aim of reconstitution is to ensure the concentration of the gelator is below that required to gel the sample, whilst at the same time ensuring a formulation for controlled release of anaesthesia, as herein described, is achieved.

Further, where a gel is present, the temperature of the solution may also affect the viscosity of the formulation and so the rate of release of the anaesthetic. Thus, in this alternative aspect, the invention is devised to work over a wide temperature range so that it can be used in a number of hostile environments from 4° C. to 40° C. Typically, the formulation is for use at a temperature of 20° C.

Additionally, in the alternative aspects or embodiments of the invention, the invention is devised to work over a wide temperature range so that it can be used in a number of hostile environments from 4° C. to 40° C. Typically, the formulation is for use at a temperature of 20° C.

In a preferred embodiment of the invention, as mentioned, the cartridge delivers sufficient anaesthetic to anaesthetise a patient for one hour, however, where circumstances demand, larger cartridges containing a larger amount of a selected formulation may be used, or a number of sequential cartridges may be used to release anaesthetic for up to any selected period equalling the sum of each single used cartridge. In either of the afore events, either, the formulation of a single cartridge when used with an adjustable stirrer or agitator is such that the initial anaesthetic dose would be limited to a maximum of 4×MAC to prevent overdose or flammability of the anaesthetic gas mixture, or, the first one or more in a series of cartridges would be limited to a maximum of 4×MAC to prevent overdose or flammability of the anaesthetic gas mixture.

In the instance where two or more cartridges are used the device construction allows for empty cartridges to be replaced during the period of anaesthesia without affecting the level of anaesthetic released. This is achieved by a quick-action release and refit mechanism for each cartridge, typically, of a conventional nature which may encompass, but is not limited to, a spring assisted mechanism, a screw fit mechanism, a trigger release mechanism, or a latch mechanism.

In any of the above aspects or embodiments of the invention said anaesthetic control release medium and said anaesthetic when mixed together in a cartridge have a surface area of 10-60 $cm^2$, including all 1 $cm^2$ increments there between, and ideally, a surface area of 20-50 $cm^2$ including all 1 $cm^2$ increments there between, and most ideally still a surface area of 50 $cm^2$. Please see FIGS. 39-40.

In any of the above aspects or embodiments of the invention said anaesthetic may be any known inhalation anaesthetic such as a fluorinated hydrocarbon, commercially known examples of which are desflurane, isoflurane, halothane, enflurane and sevoflurane. Those skilled in the art will be aware of other known anaesthetics that can be used to work the invention such as methoxyflurane.

A further advantageous feature of the invention is that at the end of the procedure a cartridge can be returned to the manufacturer and recharged with anaesthetic for subsequent use.

In yet a further aspect of the invention there is provided an inhalation device comprising: a mask for positioning over the face of a patient; a supply, or access to a supply, of breathable gas in fluid communication with said mask and at least one docking port for at least one releasable anaesthetic cartridge and further wherein said device is adapted or configured such that anaesthetic released from said cartridge is mixed with said breathable gas before being delivered to said patient.

In a preferred embodiment of the invention insertion of said cartridge into the device starts the delivery of anaesthetic or, alternatively, a valve is activated to start the delivery of anaesthetic once breathable gas is passed over or through the cartridge.

More ideally still, said afore valve, or an additional valve, is provided between said cartridge and said breathable gas supply whereby flow of said anaesthetic can be attenuated or stopped.

In a further preferred embodiment of the invention said device includes a monitor for signalling to a user that anaesthetic gas is being released from said cartridge this may be either a device that detects anaesthesia such as a colour sensitive feature or it may be a timer that is activated at the start of use of a new cartridge and so used to count the time that the cartridge should last. Alternatively, said device detects and indicates a volume change in the cartridge contents which is associated with evaporation of the anaesthetic.

In a further preferred embodiment of the invention said device is provided with a positive pressure device whereby assisted ventilation or inhalation can take place, in its simplest embodiment this is in the form of a pumpable air bag, however, it may be in the form of a mechanical, pneumatic or electronic ventilator connected to a pressurised canister of breathable gas such as oxygen, nitrous oxide or oxygen enriched air.

In a yet further preferred embodiment of the invention said breathable gas supply is either a canister as mentioned above or a vessel containing oxygen or an open-ended tube to the air.

Preferably the device of the invention is configured so the carrier gas flows either through the contents of the cartridge or over the top thereof.

More preferably still, said device comprises a closed loop circuit whereby exhaled breath from the patient is treated to first remove carbon dioxide, and then, any anaesthetic in the patient's exhaled breath is removed or recaptured for subsequent use, ideally, using natural or synthetic molecular sieves. Those skilled in the art will be aware of other conventional filters or extractors for removing carbon dioxide or anaesthetic from exhaled breath and which can be suitably deployed in the working of the invention.

More preferably again, said device comprises a pump for controlling the rate of flow of breathable gas there through, ideally but not exclusively, whereby breathable gas may be delivered at a first flow rate to induce anaesthesia and subsequently at a second flow rate to maintain anaesthesia. An example of this working arrangement is shown in FIG. 35.

This further aspect of the invention i.e. the inhalation device, may, in preferred embodiments, include or be characterised by any of the aforementioned features pertaining to the cartridge.

The formulation of the invention may be prepared by bringing into association the anaesthetic control release medium and the said anaesthetic. In general, the formulations of the invention are prepared by uniformly and intimately bringing into association the anaesthetic control release medium and the said anaesthetic.

The above formulations will generally be sterile.

In the instance where the cartridge comprises an anaesthetic control release medium such as a surfactant solution and, optionally following reconstitution of a gelled anaesthetic, a gelling agent both said surfactant and said gelling agent have non-volatile properties thus ensuring that only anaesthetic is released from the said formulation.

According to a further aspect of the invention there is provided a method of delivering volatilised anaesthetic using the cartridge of the invention in combination with an inhalation device as described herein.

Although the invention has been described with reference to human use the invention is applicable to the veterinary industry and so also comprises a cartridge modified to include a veterinary anaesthetic. Notably, whilst anaesthetic agents differ between human and veterinary use all are volatile anaesthetic agents. This means the device of the invention is useful in veterinary anaesthesia. In this application a cartridge of an appropriate size and so containing a formulation of at least one anaesthetic and anaesthetic control release medium for delivering an amount of anaesthetic to a selected animal of a particular size is provided so that the invention can be used by vets to perform operations on animals either in purpose built facilities or in situ. In a further preferred use of the invention said animal is equine, canine, feline, porcine, or any other domestic, agricultural or wild species. In use, a veterinarian will select a cartridge of appropriate MAC value or anaesthetic volume % to use on a particular animal.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described by way of example only with reference to the following figures wherein:

FIG. 5 shows that mixing the anaesthetic with a surfactant solution gives the correct release profile of a higher initial level followed by a stable lower anaesthetic concentration over an extended time-course of one hour. Sevoflurane concentration in $N_2$ carrier gas flow after gas passed at 2 L min$^{-1}$ over a formulation containing 3 ml sevoflurane dispersed at 20 wt % in a surfactant solution. The inset shows the proposed emulsion structure of dispersed droplets of anaesthetic stabilised by a layer of surfactant adsorbed at the anaesthetic/water interface;

FIG. 6 shows the chemical structures of example low molecular weight gelators that may be used to gel the anaesthetic;

Table 1 shows that the model anaesthetic molecule 2H,3H-perfluoropentane (HPFP) may be formulated to provide a high content of volatile fluorocarbon liquid by shaking the liquid with an aqueous in a surfactant solution. The hazy/opaque appearance of the samples is indicative of emulsion formation;

Table 2 shows the moderation of evaporation by formulation of the model anaesthetic liquid HPFP;

Table 3 shows how the moderation of evaporation by formulation of the model anaesthetic liquid HPFP can be further controlled by flowing the carrier gas over and especially through the sample in the testing chamber;

Table 4 shows how the concentration of volatile liquid in the carrier gas and the time taken to release all of the anaesthetic can be affected by the flow of carrier gas through the sample, and how the effects of formulation on retarding volatile release are maintained under these conditions;

Table 5 shows Zonyl FSN-100 stabilised emulsions. Tested in flow rig 6 (50 cm$^2$ surface area);

Table 6 Sevoflurane emulsions stabilised by other surfactants. Tested in flow rig 6 (50 cm$^2$ surface area) Abbreviations: Capstone FS-3100 (C); Polyfox 159 (P); Brij O20 (B);

Table 7 Effect of stirring rate on release. Tested using formulation ZS2.0 at constant temperature and flow rate in flow rig 6 (50 cm$^2$ surface area);

Table 8 Release at 4 L min$^{-1}$ flow rate. Zonyl FSN-100 stabilised emulsions tested in flow rig 6 (50 cm$^2$ surface area). Flow rate=4 L min$^{-1}$;

Table 9 Emulsions stabilised by other surfactants tested in flow rig 6 (50 cm$^2$ surface area). Flow rate=4 L min$^{-1}$ Abbreviations: Capstone FS-3100 (C); Chemguard S-550L-100 (S);

Table 10: Summary stirring rates used to generate release profile data presented in FIG. 47;

Table 11: Summary stirring rates used to generate release profile data presented in FIG. 48;

Table 12: Summary stirring rates used to generate release profile data presented in FIG. 49a; and Table 13: Summary stirring rates used to generate release profile data presented in FIG. 49b;

DETAILED DESCRIPTION OF THE INVENTION

Figure 1A:
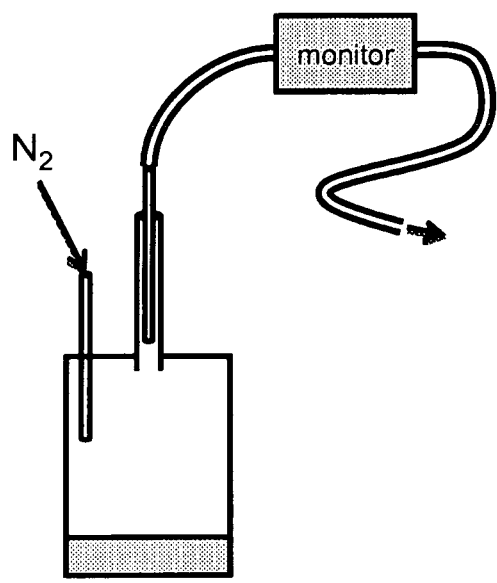
FIG. 1a shows the basic experimental testing chamber and set-up used to test the invention. Specifically, a 60 ml glass jar fitted with septum, $N_2$ inlet and 1 ml syringe (open to air). Typically tests used a 3 ml sample or equivalent with respect to anaesthetic content. Headspace concentrations were sampled from gas flow out (no recirculation) and measured with a standard anaesthetic monitor using a balloon to provide a nitrogen atmosphere or with or 2 L $min^{-1}$ $N_2$ passed over or bubbled through sample.

Sevoflurane was used as received from Abbott. 2H,3H perfluoropentane was used as received from Fluorochem UK. Zonyl FSO100 was used as received from DuPont. All water was deionised. Formulations of Sevoflurane, isoflurane or HPFP in surfactant solutions were prepared by vigorous shaking (by hand) of the required quantity of fluorocarbon with a pre-prepared aqueous surfactant solution at the proportions and concentrations described in the list of formulations described herein. The formulations described in Tables 1-4 were tested using testing chamber 1, the experimental set-up for which is described in FIG. 1a, by addition of an appropriate quantity of formulation to a 60 ml glass jar fitted with septum, $N_2$ inlet and (needle free) 1 ml syringe (open to air) via a plastic tube from within which the outflow gas was continuously sampled and monitored for anaesthetic concentration. Typically a 3 ml sample was used, or an equivalent amount with respect to anaesthetic content. A balloon was used to provide a nitrogen atmosphere with no flow-through, or a continuous flow of nitrogen as a carrier gas was passed over or bubbled through the sample at a controlled flow-rate. Headspace fluorocarbon concentrations were sampled from gas outflow (no recirculation) and measured using a standard anaesthetic monitor (Capnomac Ultima, Datex Instrumentarium Inc., Heslinki, Finland), monitoring on either sevoflurane or isoflurane settings, depending on the anaesthetic in the formulation.

Figure 1B:
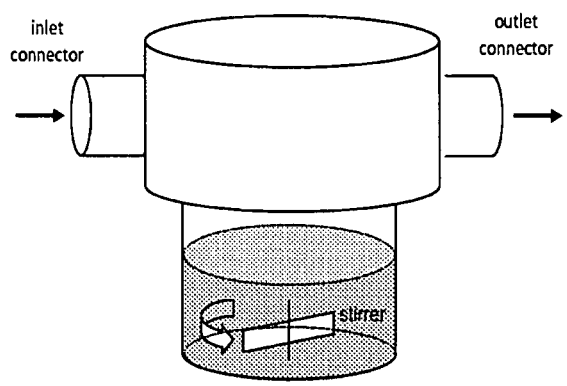
FIG. 1b shows a schematic of flow rig model 6, unless otherwise indicated surface area of formulation is 50 $cm^2$, stirrer bar is 60 mm×10 mm(diam), inlet connector is connected to the gas supply, outlet connector is connected to anaesthetic monitor.

Formulations described in tables 5 onwards were tested in the flow rig described in FIG. 1b, using different sample containers to vary the surface area where required, and using volumes as described in the tables (typically 30-120 ml). Nitrogen gas was passed through the sample chamber at a controlled flow rate, typically 1 L/min to 4 L/min, and the anaesthetic concentration in the outlet stream measured with a standard anaesthetic monitor (Capnomac Ultima, Datex Instrumentarium Inc., Heslinki, Finland), monitoring on either sevoflurane or isoflurane settings, depending on the anaesthetic in the formulation. In some instances a thermostatted cell consisting of a double-walled glass water-jacket was used, connected to a circulating water bath to maintain temperatures other that 20° C.

Making the Emulsion

The emulsions were prepared by mixing a known volume of anaesthetic with a known volume of dispersion medium. The dispersal medium, typically a surfactant solution, was pre-prepared at a known concentration of surfactant. The emulsions were formed by manual shaking of the two components for a fixed time of 60 s. More energetically intensive mixing methods, for example, high shear mixing, sonication or emulsification apparatus were not required to form the emulsions, although obviously these represent alternative preparation methods that could be employed.

Emulsion Structure Use of the Inhalation Device

The formation of an emulsion was determined by light-microscope imaging using an Olympus BX50 system microscope (Olympus, UK) fitted with JVC TK-C1380 colour video camera (JVC, Japan) and analysed using Image J software (Fiji, USA). Additional measurements were obtained from dynamic light scattering measurements using The Brookhaven ZetaPlus analyser (Brookhaven Instruments Ltd., USA). For light scattering measurements the emulsions were diluted by a factor of 20-50 depending on the emulsion concentration.

Use of the Inhalation Device

Figure 8:
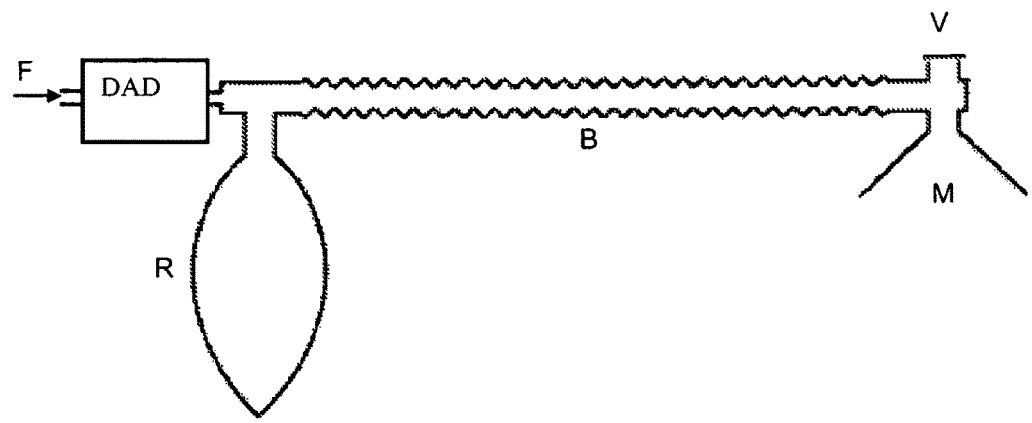
Figure 9:
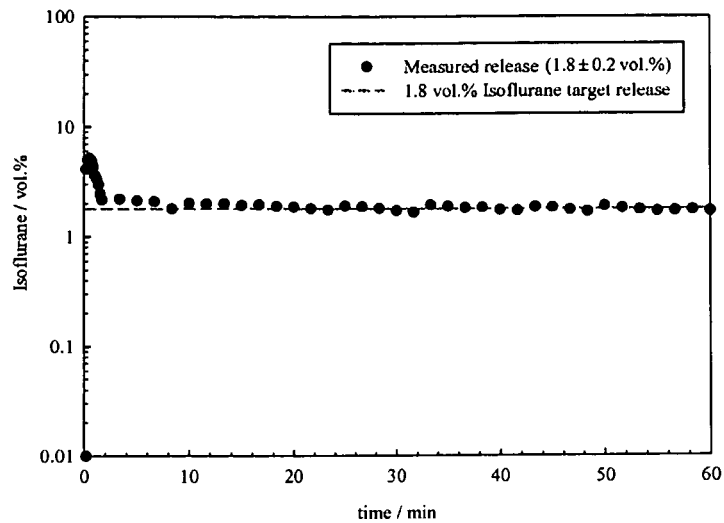
Figure 10:
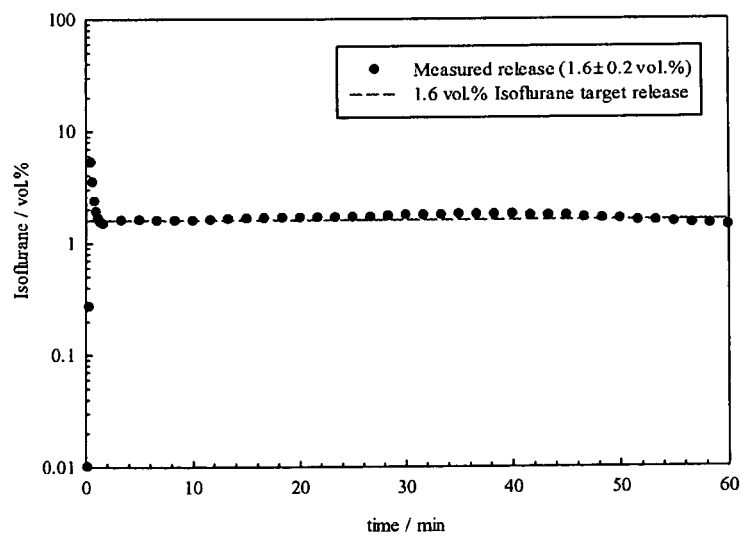
Figure 11:
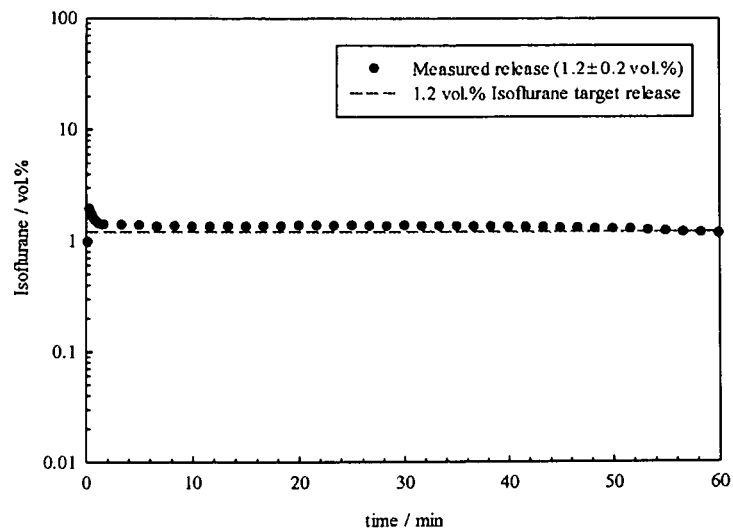
Figure 12:
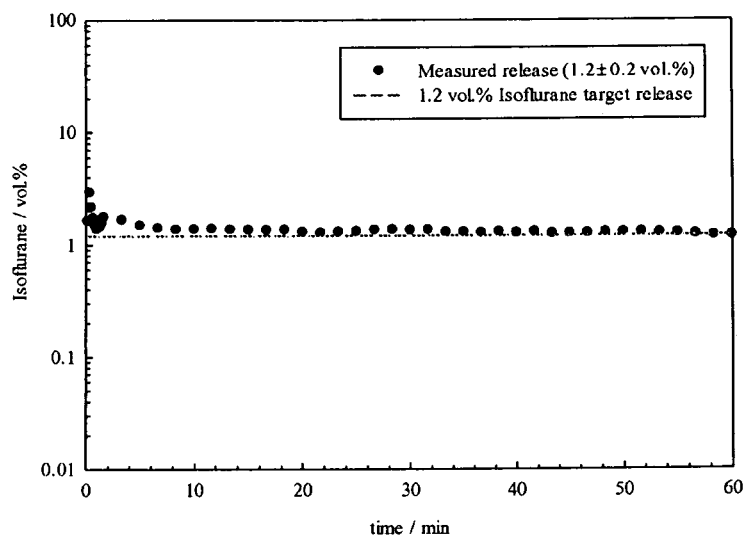
Figure 13:
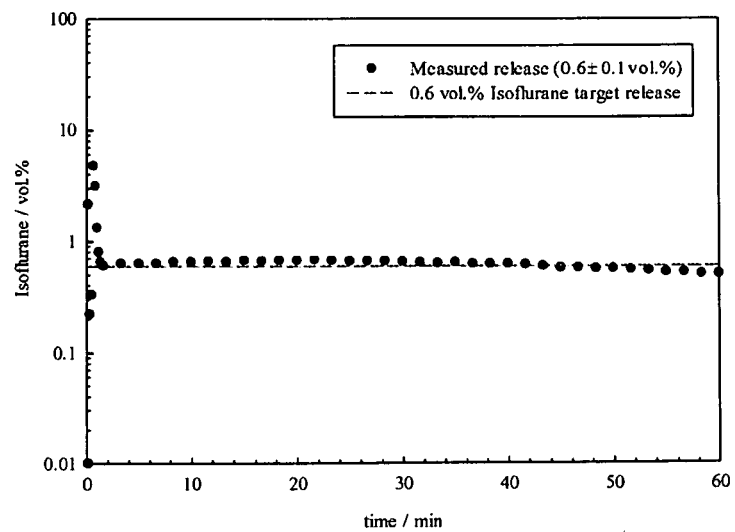
Figure 14:
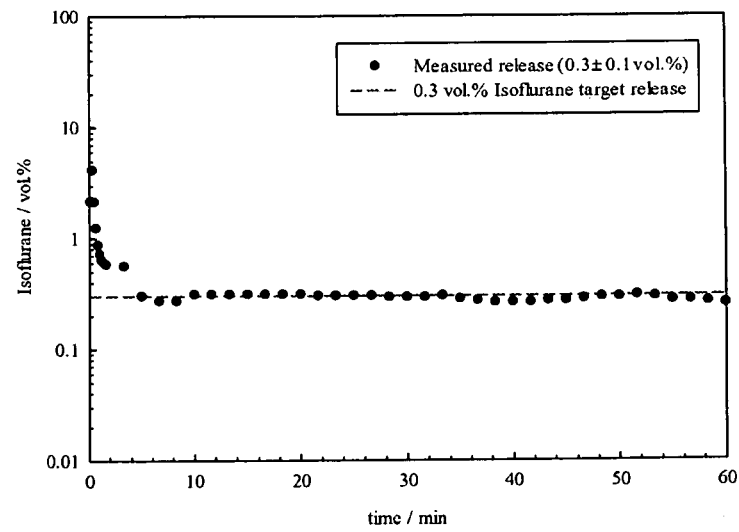
Figure 15:
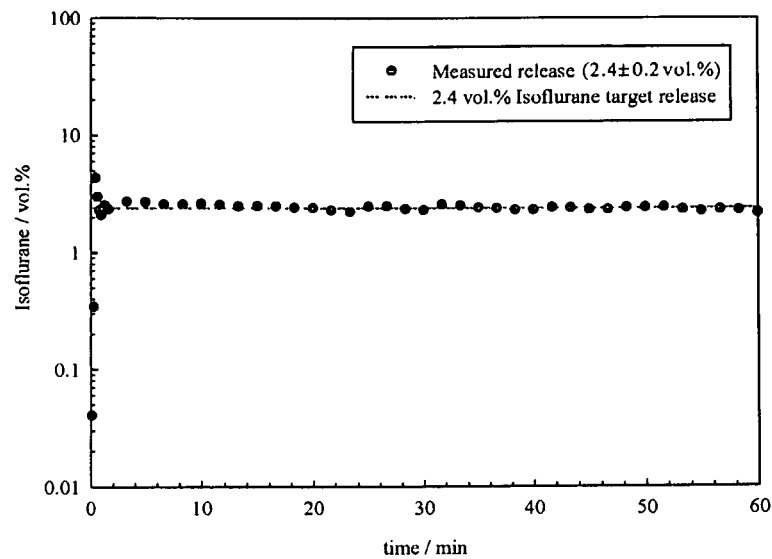

A typical inhalation device of the invention is shown in FIG. 8 it includes a supply of breathable air or gas, in this instance fresh air, and downstream thereof a releasable anaesthetic cartridge (DAD) which is connected to a conventional docking mechanism known to those skilled in the art. Although not shown, said cartridge comprises an adjustable stirring or agitation device whereby the release of anaesthetic from said cartridge can be controlled as herein described and with reference to the Figures. In the embodiment shown in FIG. 8 a reservoir bag is provided and a breathing tube is connected to a face mask. Further, in this embodiment of the invention said face mask includes a valve whereby commencement of anaesthesia can be controlled. In other embodiments of the invention said inhalation device may be connected to a supply or canister of breathable gas upstream of said releasable anaesthetic cartridge. Additionally or alternatively, said breathing tube may comprise a circular, closed system in which case a further breathing tube connects the mask with the supply of breathable gas. In this embodiment there is also provided, downstream of said face mask, filters or extractors for extracting from exhaled breath selected gases such as carbon dioxide or anaesthetic gas whereby exhaled gas can be suitably treated then recycled and reused and anaesthetic extracted from the exhaled breath may also be re-used. With the exception of the releasable anaesthetic cartridge, the configuration and components of the inhalation device are known to those skilled in the art. In use, a releasable anaesthetic cartridge is located within a corresponding connecting device and either this action of location releases anaesthetic from the cartridge or a separate valve is provided for this purpose. The mask is placed over the face of a patient and the device is ready to use. If a user wants to alter the amount of the anaesthetic released the adjustable stirrer is used to either raise or lower anaesthetic release as herein described. In the instance where a contained supply of breathable gas is used this is switched on before the face mask is placed over a patient.

Results

Figure 2:
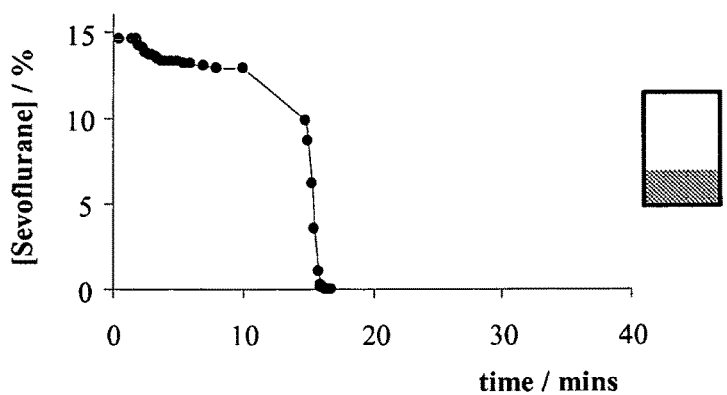
FIG. 2 shows how the uncontrolled evaporation of sevoflurane leads to dangerously high concentrations in the carrier gas and demonstrates the limited timescale over which evaporation occurs. Sevoflurane concentration in $N_2$ carrier gas flow after gas passed at 2 L $min^{-1}$ over 3 ml liquid sevoflurane. (In the inset schematic orange represents the liquid anaesthetic)

FIG. 2 shows the time dependence of the sevoflurane concentrations detected in the output carrier gas flow after addition of 3 ml sevoflurane to testing chamber 1, with carrier gas flow of 2 L min$^{-1}$ through the sample environment headspace. Clinically dangerous concentrations of anaesthetic (13-15%) were recorded in the carrier gas outflow stream for the first 10 minutes, with a sudden drop observed around 15-16 minutes until zero anaesthetic concentration is recorded. This clearly demonstrates that more control of the evaporation process is required.

Figure 3:
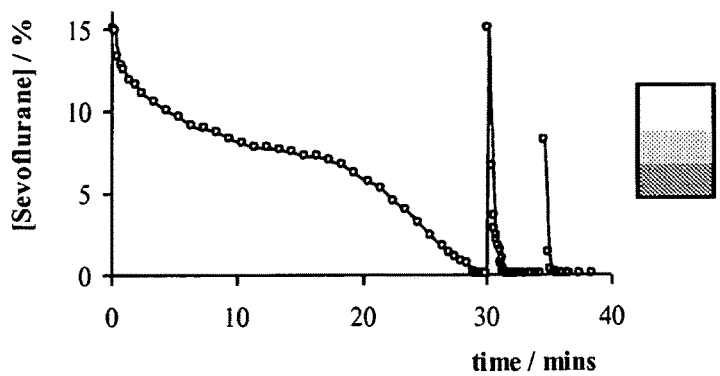
FIG. 3 shows that anaesthetic evaporation may be retarded by placing the liquid anaesthetic under a layer of water, that this prolongs the evaporation but that this system is also extremely sensitive to agitation leading to dangerously high concentrations in the carrier gas. Sevoflurane concentration in $N_2$ carrier gas flow after gas passed at 2 L $min^{-1}$ over 3 ml liquid sevoflurane in a phase separated sample with 3 ml water. Water (blue) forms the upper layer. Spikes in concentration at 30 and 36 minutes are due to shaking of the containment vessel.

FIG. 3 demonstrates that the speed of evaporation can be moderated somewhat by placing the anaesthetic under an equivalent volume of water. The anaesthetic was injected at the bottom of the containment vessel, and the natural immiscibility of the fluorocarbon and water prevents significant mixing of the two phases. 2 L min$^{-1}$ carrier gas flow was used.

FIG. 3 shows the initial measured sevoflurane concentration of 15% (too high for clinical use) decreases over the first ten minutes to a plateau value of around 8% which is maintained for approximately a further eight minutes before declining steadily to zero over the following ten minutes. The plateau value is closer to the required clinical concentration region than the un-moderated sevoflurane but is still higher than required and is not maintained for the target timescale. Also, gentle agitation of the sample causes a spike in concentration back to 15% which decays quickly back to zero over approximately two minutes. This spike is reproduced at 35 minutes, showing a lower maximum and quicker decay as the total anaesthetic content of the formulation declines. This demonstrates that a more robust formulation is required that is less sensitive to agitation and provides delivery over a longer timescale.

Figure 4:
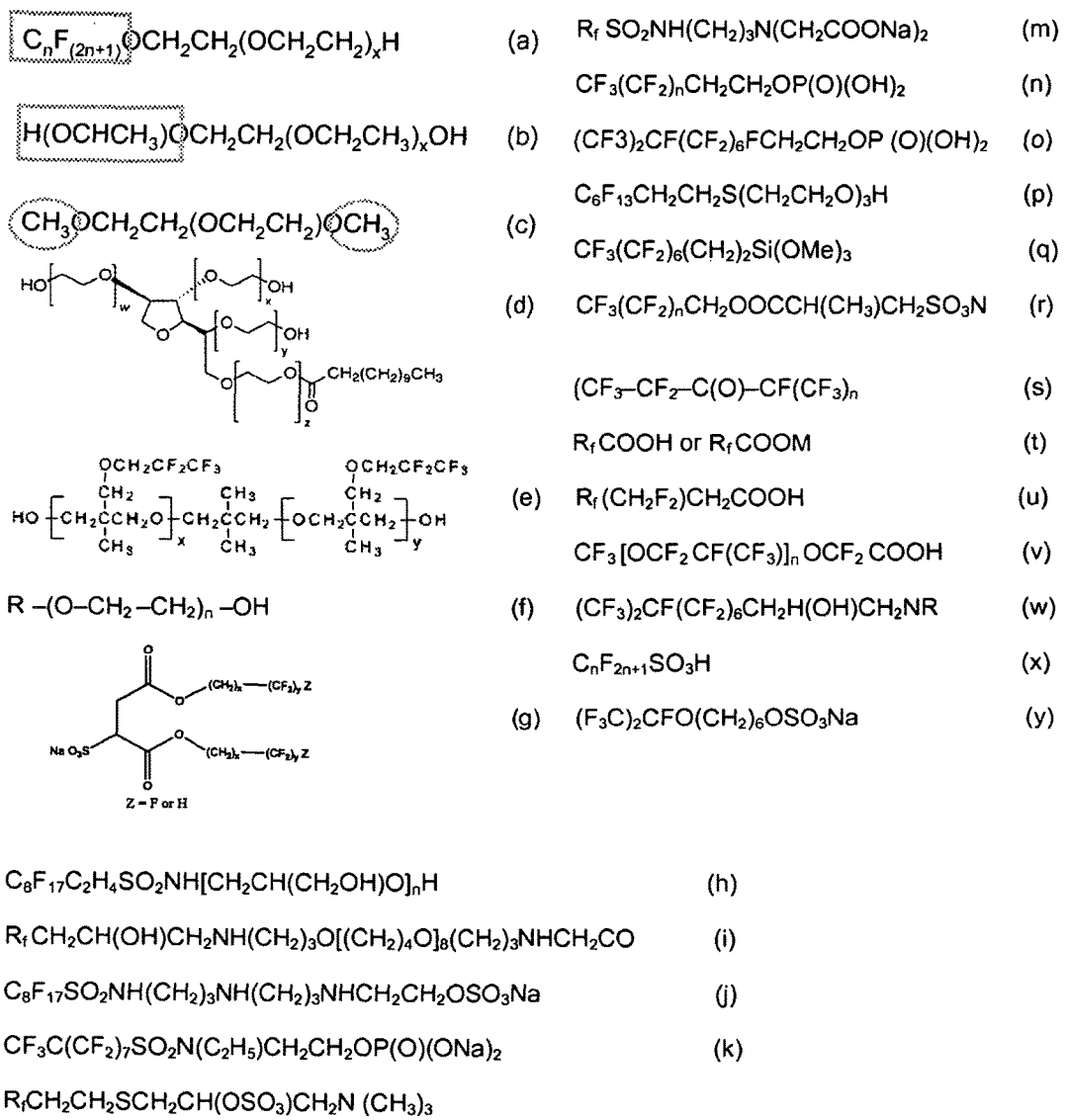
FIG. 4 shows the chemical structures of some example surfactant and polymeric stabilisers that may be used in the formulation, highlighting the functional groups useful for imparting some affinity with fluorocarbons. Structures of example classes of surfactant and polymeric stabilisers which may be used in the formulation. (a) fluorocarbon-ethylene oxide; (b) propylene oxide-ethylene oxide; (c) larger ethylene oxides with methoxy end-group functionality.

Formulation of the liquid anaesthetic by vigorous shaking with water and an appropriate stabiliser forms a hazy or opaque dispersion which phase separates over time and is therefore characteristic of emulsion formation. Some example stabilisers are shown in FIG. 4. The volatile fluorocarbon liquid 2H,3H-perfluoropentane (HPFP), which is structurally similar to sevoflurane, was used to investigate the effect of formulation parameters on evaporation rates. Table 1 and the accompanying image report the formulation of HPFP in a 10 wt % solution of Zonyl-FSO100 in water. The dispersions were readily formed by 60 seconds of manual shaking, at HPFP concentrations of between 9 and 50% v/v HPFP (equivalent to 3-15% w/w). The release properties of these formulations are summarised in Tables 2 and 3, which report the fluorocarbon concentration recorded (monitoring as sevoflurane, and therefore representing only a relative value for HPFP) at a fixed time-point of 30 s, and also the time for the measured value to drop to zero. Table 2 reports these values for two example formulations, along with the values for an equivalent amount of the unformulated HPFP. Here, the evaporation was monitored under minimal gas flow through the sample (by attachment of a balloon to provide a small positive carrier gas pressure). These data demonstrate that whether or not the liquid is incorporated into an emulsion, higher volatile fluorocarbon levels and longer time to zero gas phase concentrations are recorded where there is a larger amount of the fluorocarbon to begin with. Comparing the measured values between the unformulated and formulated HPFP, significantly lower measured carrier gas concentrations are observed for the formulations, while the degree of suppression is fluorocarbon content dependent (a 50× reduction occurs for formulation J1 (5% v/v HPFP) compared to 17× for formulation J5 (29% v/v HPFP)). Table 2 also demonstrates a greater than fourfold increase in the time to zero measured concentration for formulation J1 compared to the equivalent amount of free fluorocarbon, and the 6× higher HPFP content of J5 extended the time to zero measured concentration to greater than the maximum recorded experiment time of 20 minutes.

Repeating the experiment with formulation J5 (30% v/v HPFP) under 2 L $min^{-1}$ carrier gas flow through and over the sample highlights further the influence of formulation; Table 3 includes data for both free HPFP and HPFP under water as comparators. At 30 s the measured equivalent sevoflurane concentration is reduced by a factor of just under two by a layer of water, and by a factor of four by formulation as an emulsion. The time to zero concentration is also significantly extended, by around 25% by the water alone, but by greater than 500% by the emulsification process (experiment terminated at 25 minutes). Table 3 also demonstrates that the release can be accelerated by flowing the carrier gas through rather than over the sample, with fourteen times higher fluorocarbon concentrations recorded at the 30 s time point and a greater than three-fold reduction in the time to zero measured concentration. These data are consistent with the results of a cumulative release calculation, which indicate that >99% of the volatile fluorocarbon is released from the formulation. Hence for equivalent fluorocarbon content, a higher gas-phase concentration results in a shorter time to zero concentration, and for an equivalent volume of formulation, a higher fluorocarbon content increases both of these parameters.

The influence of gas-flow rate when using the rig shown in FIG. **1*a*** is further demonstrated by the data in table 4 which shows the effect of gas flow rate through the sample for HPFP under water and a 30% HPFP emulsion formulation. These data show that the time to zero recorded HPFP concentration is decreased with increased flow rate, as is the concentration recorded at a fixed time point of 30 s. For the formulation the time to zero measured concentration halves from 0 to 2 L$^{-1}$ gas flowed through.

Sevoflurane Experiments

FIG. 5 shows the time dependence of sevoflurane release from an emulsion formulation containing 20 wt % sevoflurane dispersed by shaking in a 10 wt % solution of Zonyl FSO-100. Comparing the overall shape of the profile to that in FIG. 2 it is evident that the retardation of the evaporation leads to an extended plateau region where a constant sevoflurane concentration in the carrier-gas is recorded. This plateau region is much lower in concentration than for either the free sevoflurane control sample (~13%, FIG. 2) or the sevoflurane under water control sample (~8%, FIG. 3). At <1% the concentration delivered from the formulation is lower than the required clinical window (~4%), however optimisation of the formulation and gas-flow conditions can be used to obtain the desired concentration. The initial concentration is also lowered by formulation (~5% sevoflurane during initialisation for the formulation, compared to ~15% for the controls), obtaining a value much closer to the clinically required concentration of around 8%. The current formulation is also successful in delivering the anaesthetic over a one-hour timescale, and therefore is a clear lead candidate for optimisation towards a clinically viable dispersion.

FIG. 6 gives the chemical structures of example low molecular weight organogelators: molecules that are known to gel organic and/or fluorocarbon liquids. Gelation of the anaesthetic therefore represents an alternative method to controlled anaesthetic release.

Figure 7:
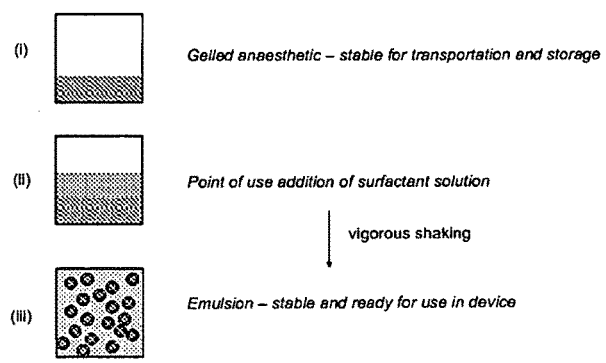
FIG. 7 shows a schematic representation of a two-stage formulation which combines the stable storage and transport properties of a gel, and is converted to an emulsion system by mixing with an aqueous solution of the FIG. 27: Sevoflurane release profile of a formulation containing 20 mL Sevoflurane and 110 mL of aqueous solution of 10 wt. % POLYFOX 159, the stirring rate was increased periodically by 50 rpm every 15 minutes to maintain a sustained Sevoflurane release of 2±0.2 vol. % after the first ten minutes for about 90 minutes under Nitrogen flow rate of 1 L min$^{-1}$ using Flow-Rig Model 6 (S.A.=50 cm$^2$), an average release of 2±0.2 vol. % (1 MAC) Sevoflurane was attained.

FIG. 7 shows a schematic representation of a two stage formulation that combined the expected formulation robustness of a gelled anaesthetic for transportation and storage, which can be converted at the point of use into an emulsion by vigorous shaking with an aqueous solution of the emulsifier (surfactant solution).

Sustained Isoflurane Release Formulations

Sustained Isoflurane release at a constant rate (MAC) (vol %) for 1 hour has been achieved at 0.3% (MAC 0.25), 0.6% (MAC 0.5), 1.2% (MAC 1), 1.6% (MAC 1.33), 1.8% (MAC 1.5) and 2.4% (MAC 2) using the formulations described in table 5, under the conditions also described therein. Graphs for each individual release profile are shown in FIGS. 9-15.

Figure 16:
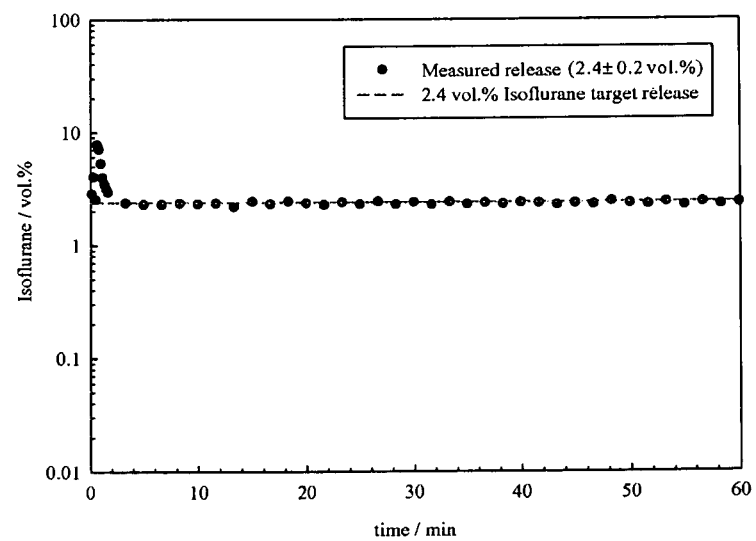
Figure 17:
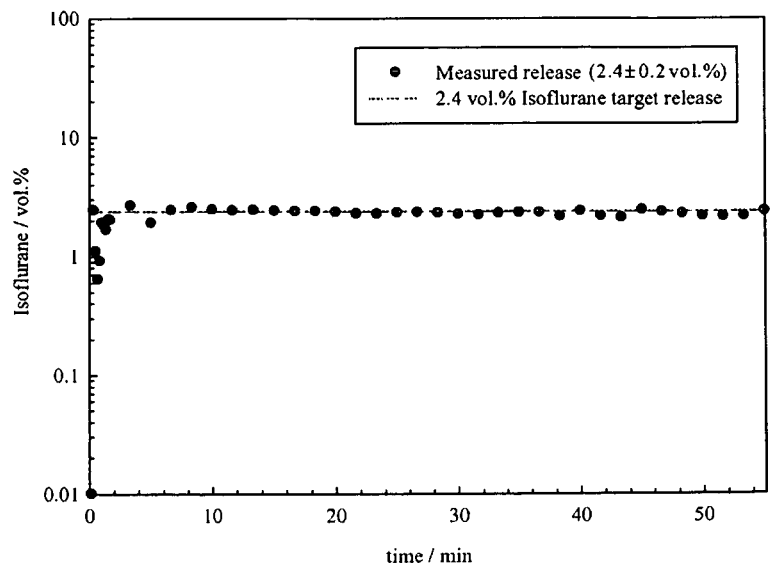
Figure 18:
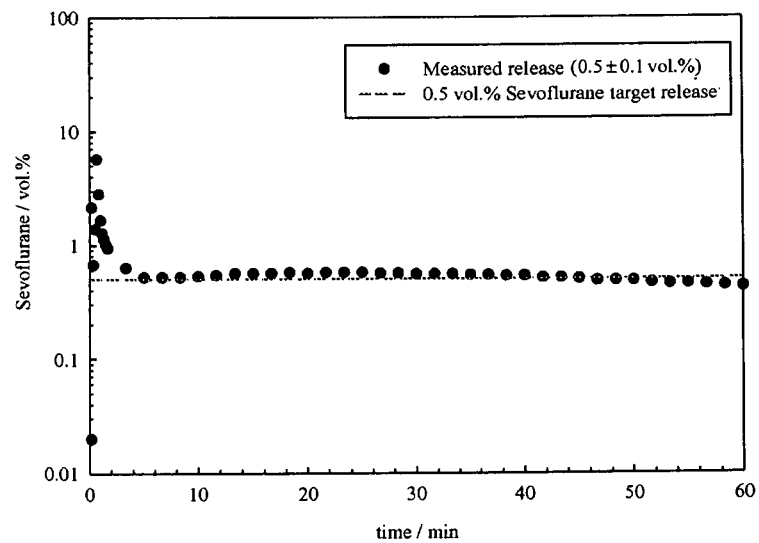
Figure 19:
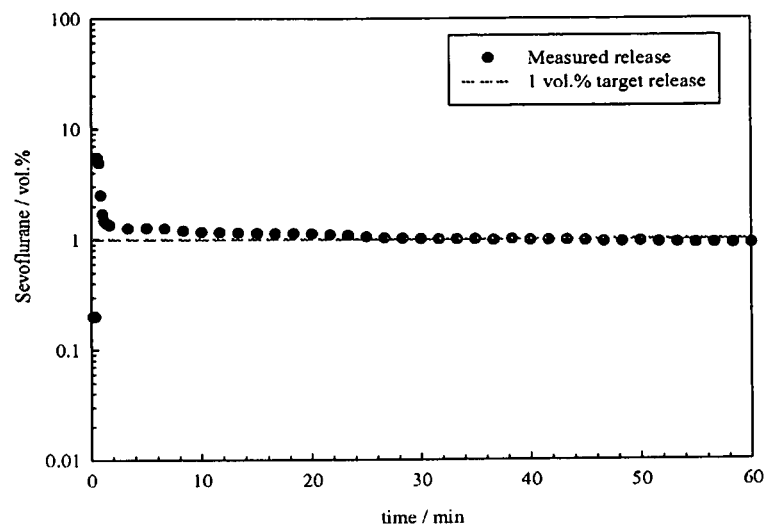
Figure 20:
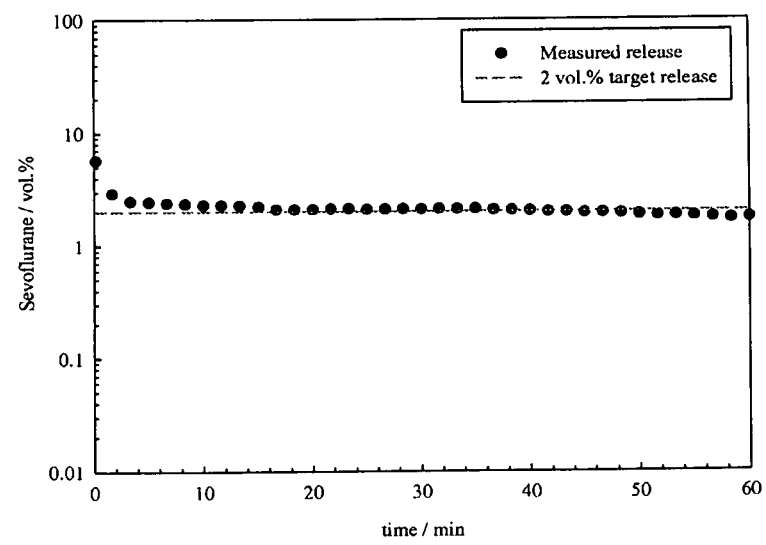
Figure 21:
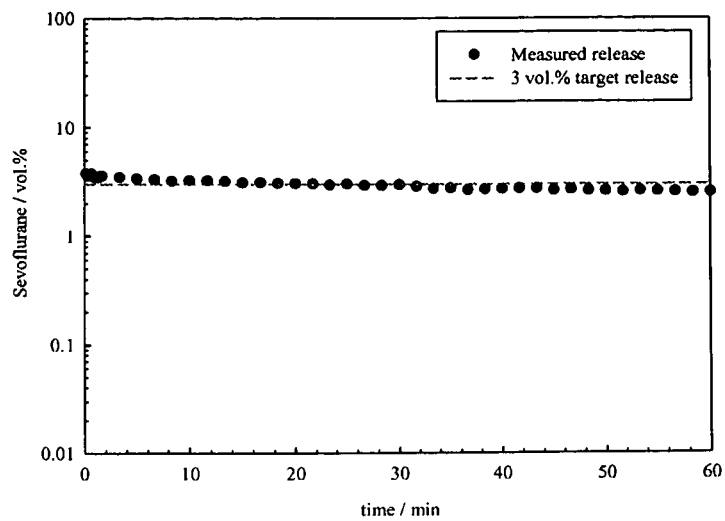
Figure 22:
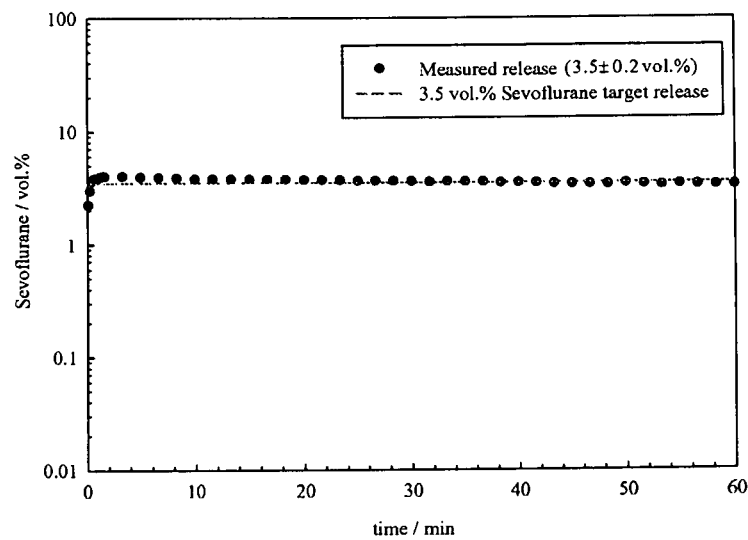
Figure 23:
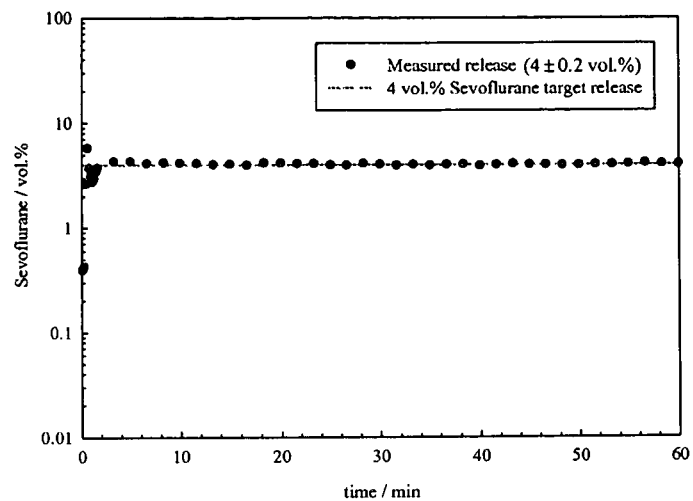
Figure 24:
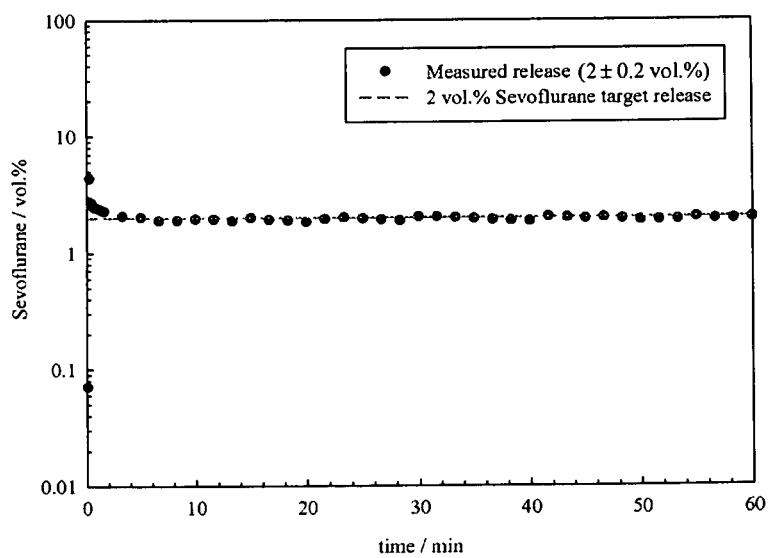
Figure 25:
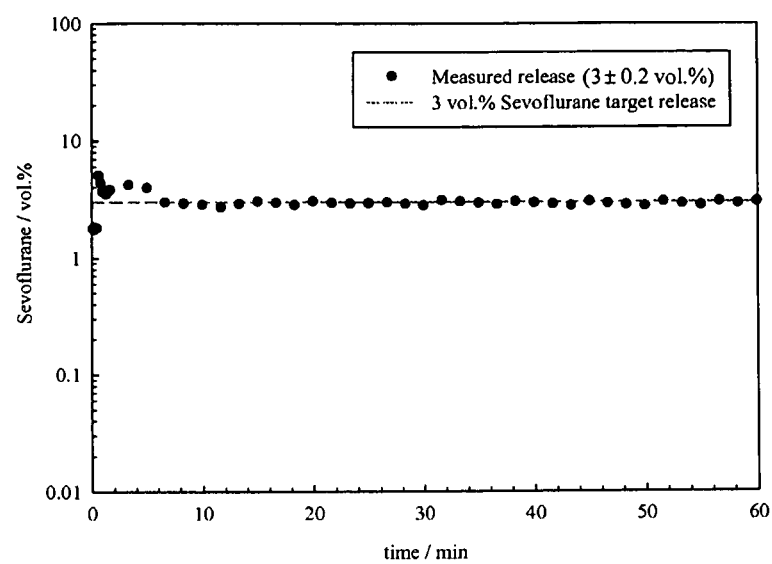
Figure 26:
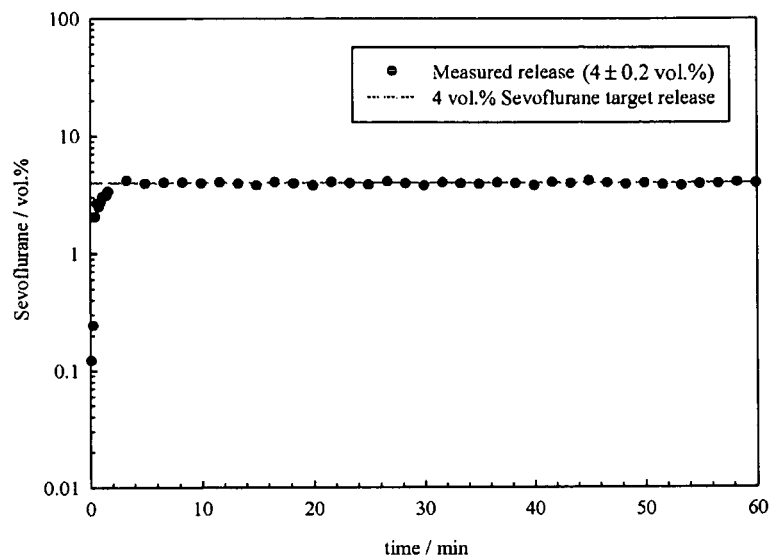
Figure 27:
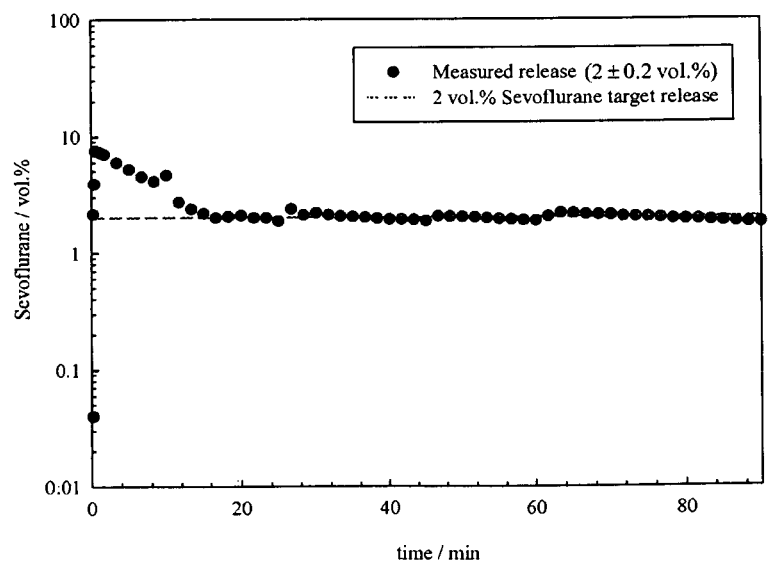
Figure 28:
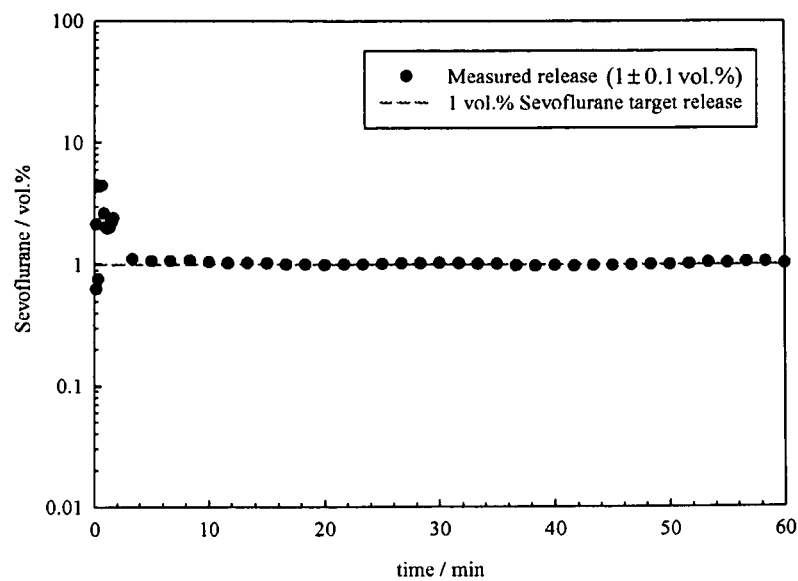
FIG. 28: Sevoflurane release profile of a 130 mL formulation containing 15 mL Sevoflurane and 115 mL of aqueous solution containing 5 wt. % Capstone FS-3100 and 3 wt. % of Polyfox 159 stirring at 230 rpm under Nitrogen flow rate of 1 L min$^{-1}$ using Flow-Rig Model 6 (S.A.=50 cm$^2$), an average release of 1±0.1 vol. % (0.5 MAC) Sevoflurane was attained.
Figure 29:
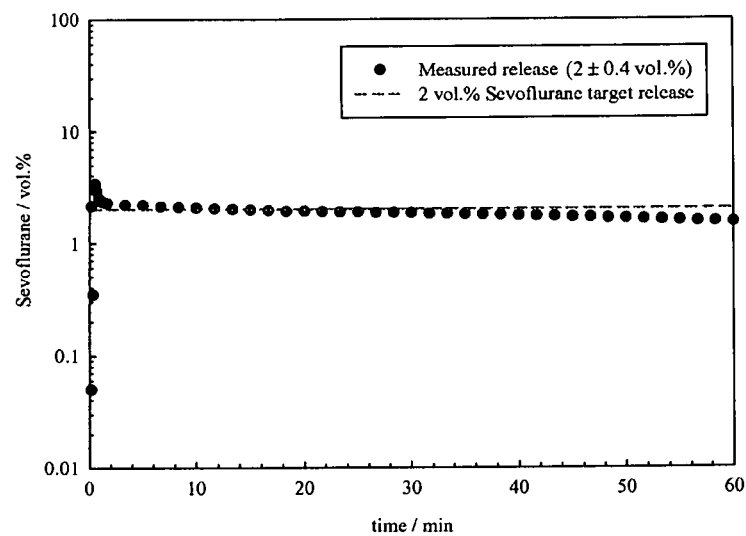
FIG. 29: Sevoflurane release profile of a 130 mL formulation containing 15 mL Sevoflurane and 112.5 mL of aqueous solution containing 10 wt. % Polyfox 159 and 3 wt. % Capstone FS-3100 stirring at 250 rpm under Nitrogen flow rate of 1 L min$^{-1}$ using Flow-Rig Model 6 (S.A.=50 cm$^2$), an average release of 2±0.2 vol. % (1 MAC) Sevoflurane was attained.
Figure 30:
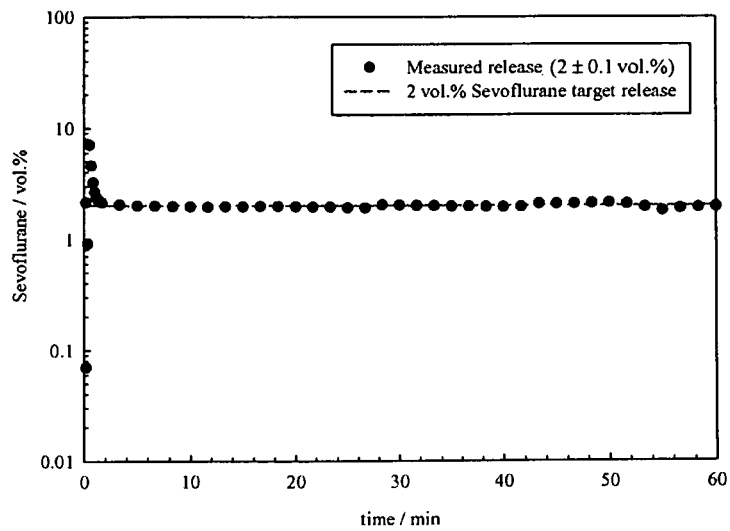
FIG. 30: Sevoflurane release profile of a 130 mL formulation containing 18 mL Sevoflurane and 115 mL of aqueous solution containing 9 wt. % Capstone FS-3100 and 5 wt. % of Polyfox 159 under Nitrogen flow rate of 1 L min$^{-1}$ and the stirring rate was increased gradually from 230-250 rpm using Flow-Rig Model 6 (S.A.=50 cm$^2$), an average release of 2±0.1 vol. % (1 MAC) Sevoflurane was attained.
Figure 31:
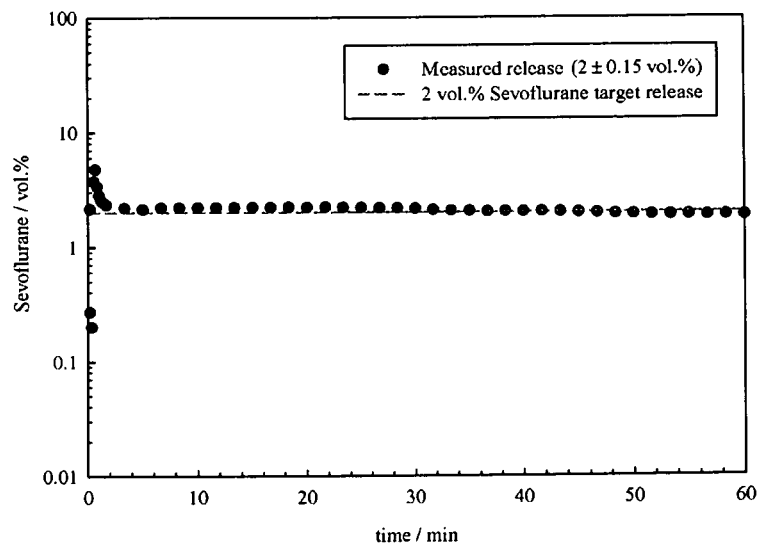
FIG. 31: Sevoflurane release profile of a 130 mL formulation containing 20 mL Sevoflurane and 110 mL of aqueous solution containing 1 wt. % Brij O20 and 12 wt. % Capstone FS-3100, stirring at 250 pm under Nitrogen flow rate of 1 L min$^{-1}$ using Flow-Rig Model 6 (S.A.=50 cm$^2$), an average release of 2±0.15 vol. % (1 MAC) Sevoflurane was attained.

Sustained Isoflurane release at a constant rate (MAC) (vol %) for 1 hour has been achieved at 2.4% (MAC 2) using the formulations described in table 8, under the conditions also described therein. Graphs for each individual release profile are shown in FIGS. 16-17.

Sustained Sevoflurane Release Formulations

Sustained Sevoflurane release at a constant rate (MAC) (vol %) for 1 hour has been achieved at 0.5% (MAC 0.25), 1.0% (MAC 0.5), 2% (MAC 1), 3% (MAC 1.5), 3.5% (MAC 1.75) and 4% (MAC 2) using the formulations described in table 5, under the conditions also described therein. Graphs for each individual release profile are shown in FIGS. 18-23.

Sustained Sevoflurane release at a constant rate (MAC) (vol %) for 1 hour has been achieved at 0.5% (MAC 0.25), 2% (MAC 1), 3% (MAC 1.5) and 4% (MAC 2) using the formulations described in table 8, under the conditions also described therein. Graphs for each individual release profile are shown in FIGS. 24-26 and FIG. 36 (1 l/min) and FIG. 41 (4 l/min).

Sustained Mixed Surfactant Release Formulations

Sustained mixed surfactant release formulations at a constant rate (MAC) (vol %) for 1 hour has been achieved at 2% (MAC 1) and 1.0% (MAC 0.5) using the formulations described in table 6, under the conditions also described therein. Graphs for each individual release profile are shown in FIGS. 27-32.

Figure 32:
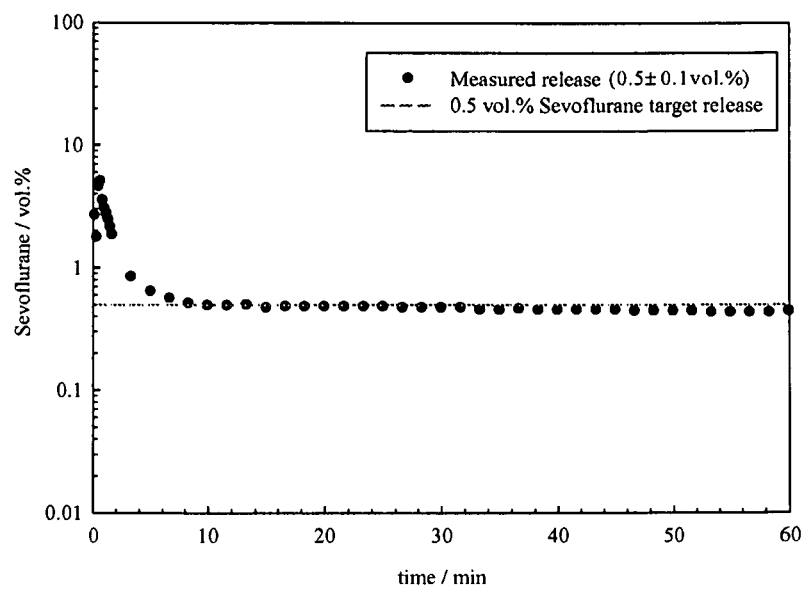
FIG. 32. Sevoflurane release profile of a formulation containing 5 mL Sevoflurane and 15 mL of 20 wt. % Brij O5 and 30 mL of 7 wt. % Tween 20 under Nitrogen flow rate of 1 L min$^{-1}$ and stirring at 200 rpm using Flow-Rig Model 6 (S.A.=50 cm$^2$), an average release of 0.5±0.1 vol. % (0.25 MAC) Sevoflurane was attained.

Sustained Sevoflurane release at a constant rate (vol %) for 1 hour has been achieved at 0.5% (0.25 MAC) under Nitrogen flow rate of 1 L min$^{-1}$ using a formulation containing 5 mL Sevoflurane and 15 mL of 20 wt. % Brij O5 and 30 mL of 7 wt. % Tween 20 and stirred at 200 rpm. The release profile is shown in FIG. 32. This figure demonstrates that hydrogenated surfactants could be used to stabilize Sevoflurane dispersions in aqueous solutions.

Formulation Reproducibility

Figure 33:
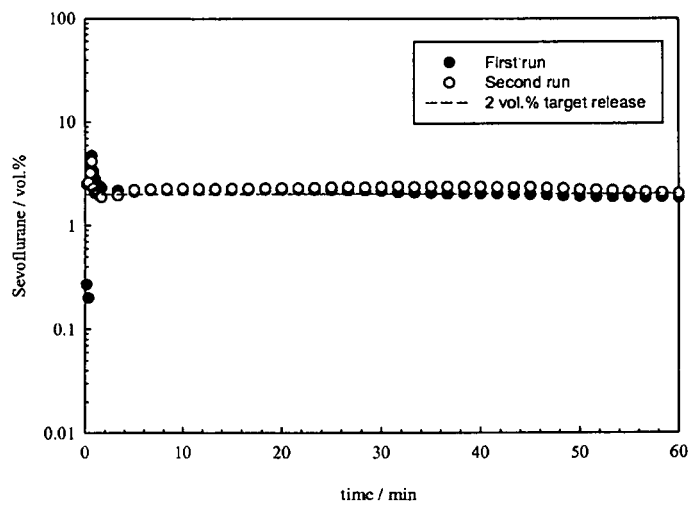
FIG. 33: Sevoflurane release profile of two 130 mL formulations containing 20 mL Sevoflurane and 110 mL of aqueous solution containing 10 mL of 10 wt. % Brij O20 and 10 mL of Capstone FS-3100 stirring at 250 rpm under Nitrogen flow rate of 1 L min$^{-1}$ using Flow-Rig Model 6 (S.A.=50 cm$^2$)
Figure 34:
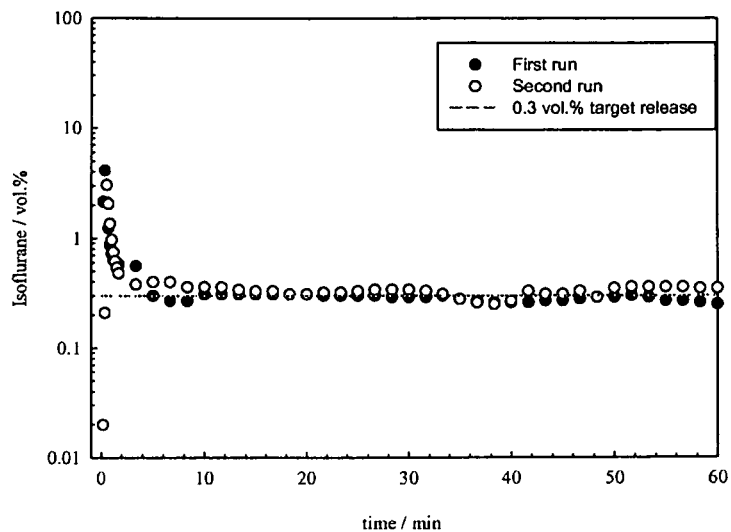
FIG. 34: Isoflurane release profile of two formulations containing 2.5 mL Isoflurane and 77.5 mL of aqueous solutions of 13 wt. % Zonyl FSN-100 stirring at 150 rpm under Nitrogen flow rate of 1 L min$^{-1}$ using Flow-Rig Model 6 (S.A.=50 cm$^2$)

Reproducibility of formulation performance is shown in FIGS. 33-34. The reproducibility of sample preparation has been demonstrated. FIGS. 33 and 34 show, for sevoflurane and isoflurane, respectively, data obtained from two replicate samples prepared independently.

Effect of Carrier Gas Flow Rate on Sevoflurane Release Profile

Figure 35:
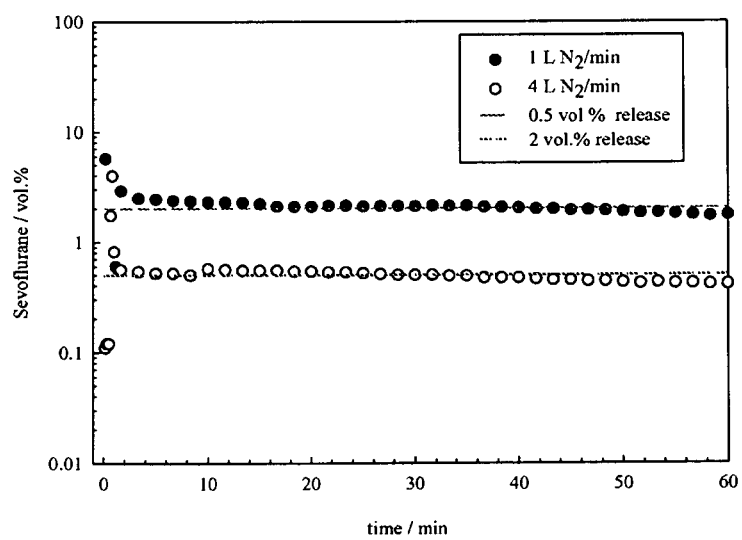
FIG. 35: Effect of Nitrogen flow rate on Sevoflurane release profile of a formulation containing 15 mL Sevoflurane and 105 mL of aqueous solutions of 7 wt. % Zonyl FSN-100 under Nitrogen flow rate of 1 and 4 L min$^{-1}$ and stirring at 250 rpm using Flow-Rig Model 6 (S.A.=50 cm$^2$)

The effect of the carrier gas flow rate on the released Sevoflurane concentration has been investigated at two different flow rates of 1 L min$^{-1}$ and 4 L min$^{-1}$ Nitrogen, using fixed-composition formulations, fixed stirring rates and using the rig shown in FIG. 1b. The resulting Sevoflurane release profiles are given in FIG. 35. As shown, increasing the flow rate of the carrier gas results in a decrease in the concentration of the released Sevoflurane, but the level remains constant over the one hour time course. In this instance the level of release obtained is 0.5MAC which is suitable for sedation purposes. This demonstrates that a chosen cartridge may be used for either anaesthesia or sedation, depending on the clinical set-up and therefore flow rate.

Emulsion Structure

Emulsion structure was confirmed and evaluated by optical microscopy and subsequent image analysis. Micrographs for 1, 2 and 3% formulations showed a droplet size of 1.5 μm, 1.4 μm and 1.4 μm, respectively. These results and the droplet size of the other formulations are shown in tables 5, 6, 8 & 9.

Effect of Stirring Rate on Sevoflurane Release Profile

It has been demonstrated that stirring rate can be used to alter and control Sevoflurane release from the formulation.

Figure 36:
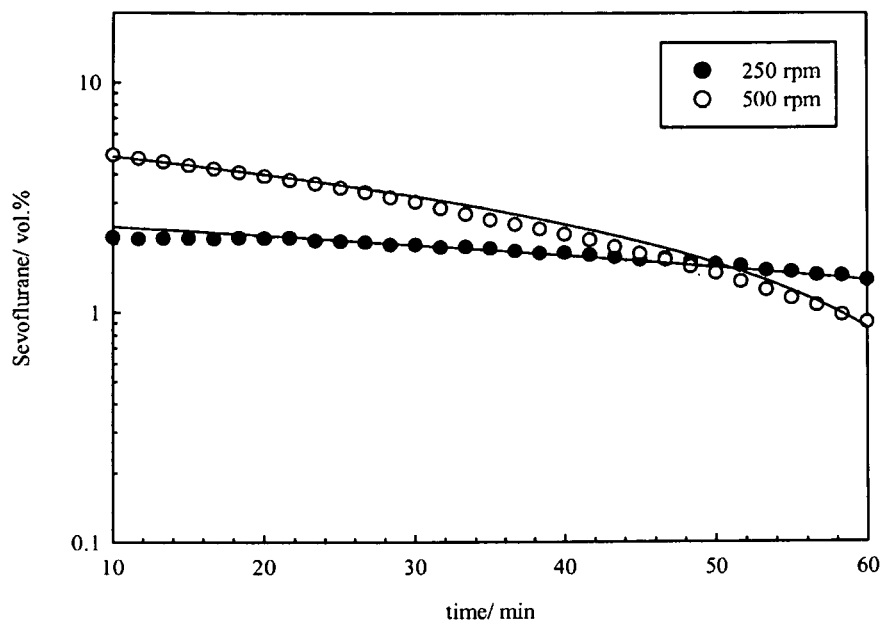
FIG. 36: Effect of stirring rate on Sevoflurane release profile of a formulation containing 15 mL Sevoflurane and 105 mL of aqueous solutions of 7 wt. % Zonyl FSN-100 under Nitrogen flow rate of 1 L min$^{-1}$ and stirring at 250 and 500 rpm using Flow-Rig Model 6 (S.A.=50 cm$^2$)

For a formulation that gives a steady release, e.g. at 2% with a stirring rate of 250 rpm, using a higher stirring rate 500 rpm causes an increase in the initial release. As shown in FIG. 36, the Sevoflurane is used more quickly at the higher stirring speed and the release level drops more quickly than at slower speeds.

Different Stirring Rates within the Same Run

Figure 37:
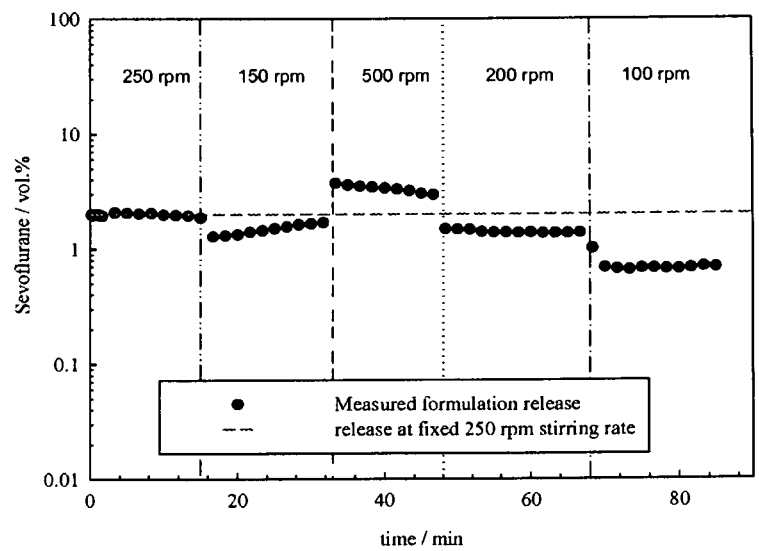
FIG. 37: Effect of stirring rate on Sevoflurane release profile of a formulation containing 15 mL Sevoflurane and 105 mL of aqueous solutions of 7 wt. % Zonyl FSN-100 under Nitrogen flow rate of 1 L min$^{-1}$ and different stirring speeds using Flow-Rig Model 6 (S.A.=50 cm$^2$)
Figure 38:
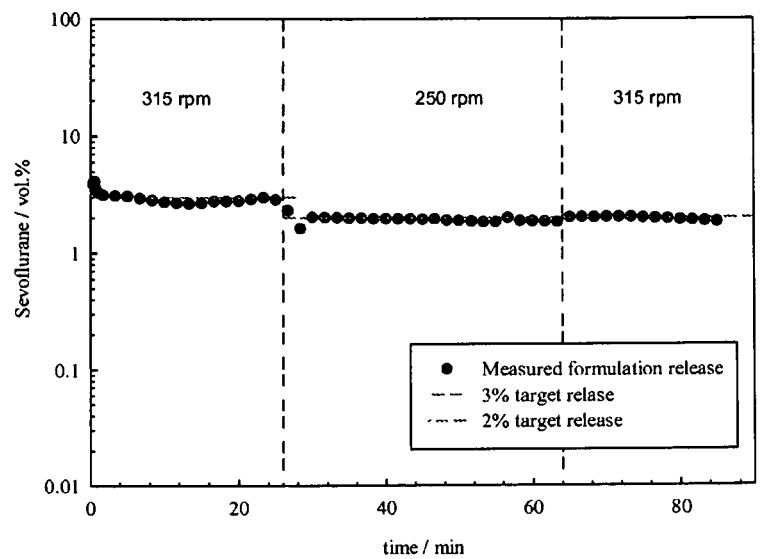
FIG. 38: Sevoflurane release profile of a formulation containing 20 mL Sevoflurane and 120 mL of aqueous solutions of 7 wt. % Zonyl FSN-100 under Nitrogen flow rate of 1 L min$^{-1}$ and stirring speed of 315 rpm for 30 minutes and then at 250 rpm for another minutes and finally at 315 using Flow-Rig Model 6 (S.A.=50 cm$^2$)

Stirring rate can be used to control the release level of Sevoflurane, and the response to stirring is both rapid and reversible, as shown in FIG. 37. FIG. 38 shows that stirring rate can be used to provide different release regimes over a one hour time-course, or to maintain a 2% release profile with <0.1% drift over a longer timescale of 80 minutes (Compare to 250 rpm data in FIG. 36). The magnetic stirrer bar used was 10 mm (diameter) by 60 mm.

Effect of Surface Area of Flow-Rig Models on Sevoflurane Release Profile

Figure 39A:
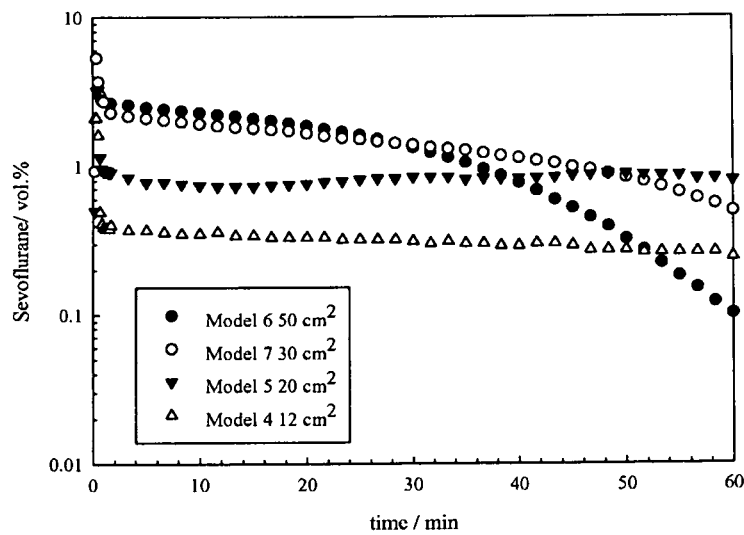
FIG. 39: (a) Sevoflurane release profiles of 50 mL formulations containing 6 mL Sevoflurane and 34 mL of aqueous solutions of 6.5 wt. % Zonyl FSN-100 under Nitrogen flow rate of 1 L min$^{-1}$ and stirring at 250 rpm using Flow-Rig Models 4, 5, 6 and 7 with surface areas of 12.5, 20, 50 and 30 cm$^2$, respectively. (b) Data at 10 and 30 min recast as function of surface area.
Figure 39B:
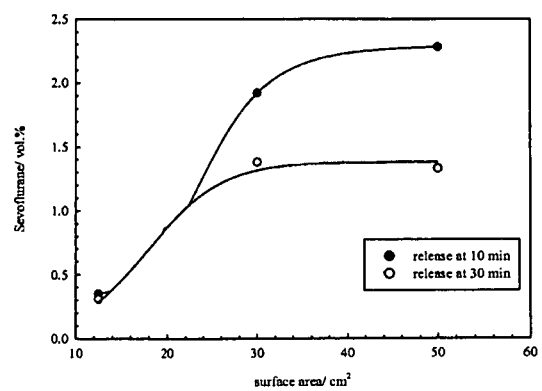
Figure 40:
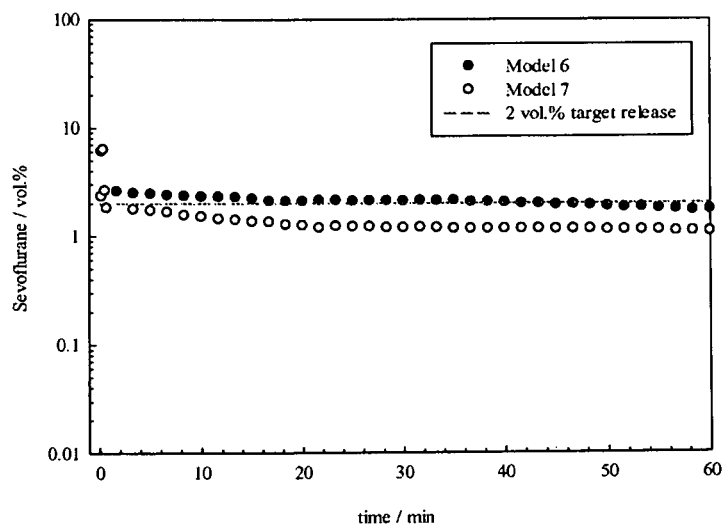
FIG. 40: Sevoflurane release profiles of formulations containing 15 mL Sevoflurane and 105 mL of aqueous solutions of 7 wt. % Zonyl FSN-100 under Nitrogen flow rate of 1 L min$^{-1}$ and stirring at 250 rpm using Flow-Rig Model 6 vs. Model 7.

The importance of using the correct surface area is demonstrated in FIG. 39(a), using a smaller amount of the 2% formulation (50 ml) to be able to compare all of the surface areas. At high surface areas the release is higher, but at low surface areas clinically required levels are not reached. Selected data points are recast in FIG. 39(b), to show that the effect of increasing surface area levels off at ~somewhere between 20 and 40 cm². A full comparison of data at 30 cm² and 50 cm² is shown in FIG. 40.

Effect of Amount of Formulation Used on Sevoflurane Release Profile

Figure 41:
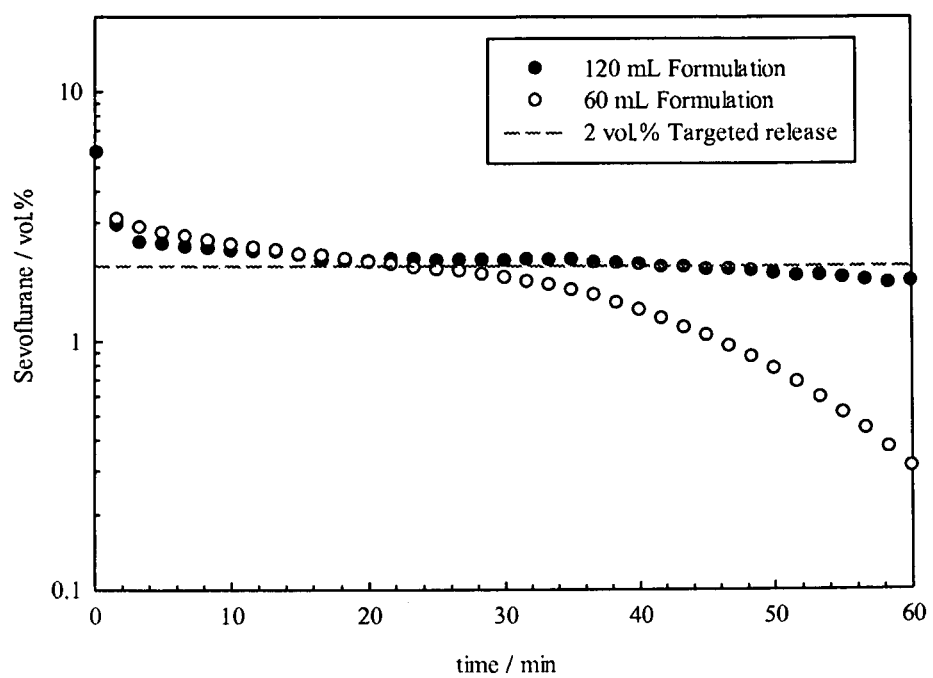
FIG. 41: Sevoflurane release profiles of 60 and 120 mL formulations containing 7.5 and 15 mL Sevoflurane and 52.5 and 105 mL of aqueous solutions of 6.5 wt. % Zonyl FSN-100 under Nitrogen flow rate of 1 L min$^{-1}$ and stirring at 250 rpm using Flow-Rig Model 6 (S.A.=50 cm$^2$)

Increasing the amount of formulation present does not significantly increase the level of release, but extends the timescale over which the level of release is sustained. This is shown in FIG. 41 for the 2% formulation.

Formulation Recycling

Figure 42:
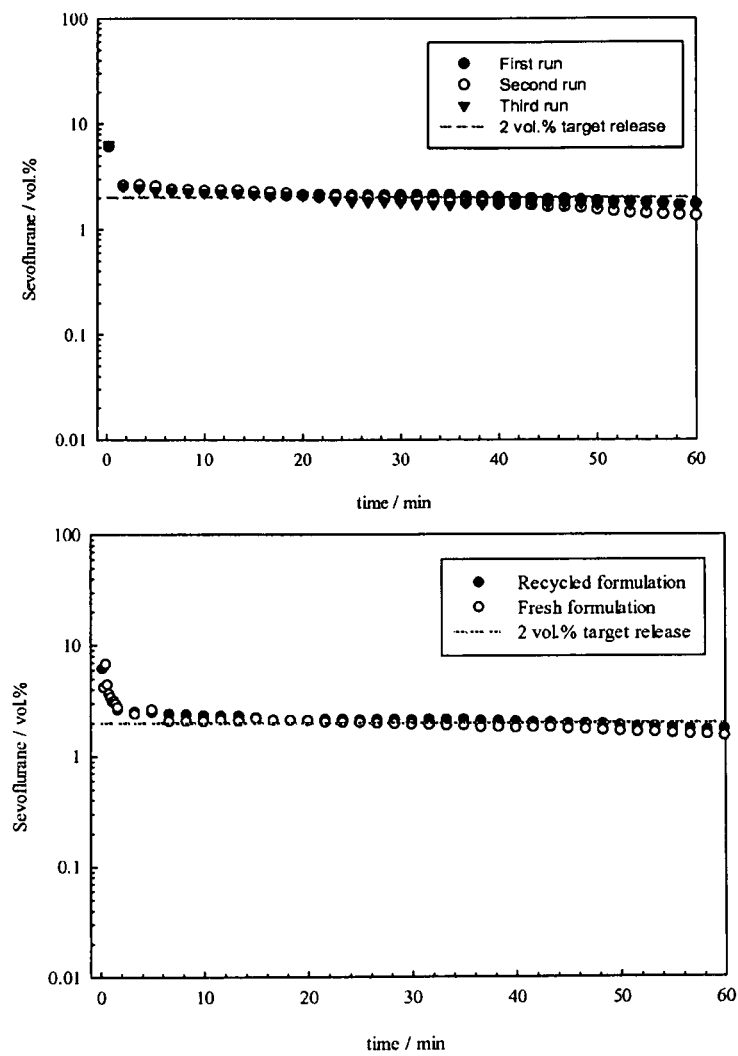
FIG. 42: Sevoflurane release profiles of different runs of a fixed composition formulation containing 20 mL Sevoflurane and 120 mL of aqueous solutions of 7 wt. % Zonyl FSN-100 under Nitrogen flow rate of 1 L min$^{-1}$ and (a) stirring at 250 rpm using Flow-Rig Model 6 (S.A.=50 cm$^2$); (b) stirring speed of 250 rpm for 30 minutes and then at 315 rpm, the recycled formulation has been employed for 10 experiments.

The formulation can be used and recharged with Sevoflurane (compensating for loss of water) with no compromise in performance, as shown in FIG. 42. The data presented are for a fresh formulation, and one employed for up to 10 experiments.

Effect of Temperature on Anaesthetic Release

Figure 43:
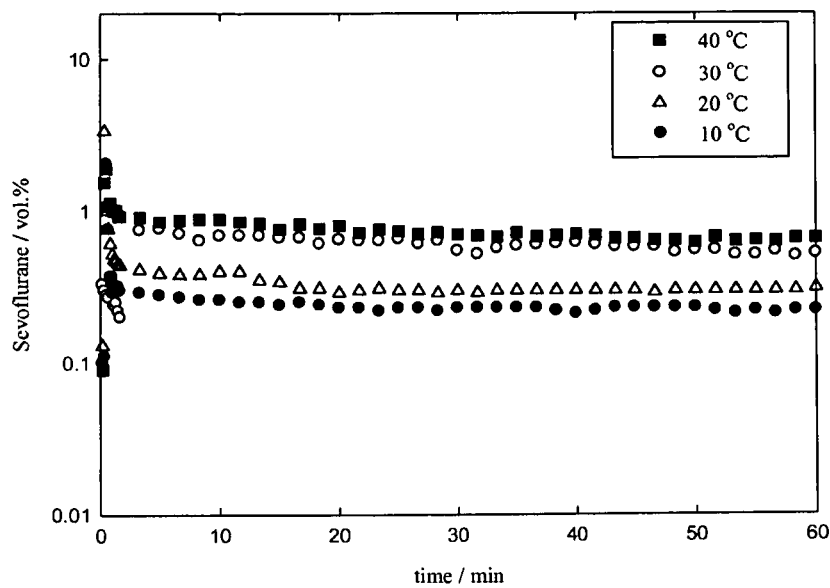
FIG. 43: Effect of temperature on Sevoflurane release profile of formulations containing 15 mL Sevoflurane and 55 mL of aqueous solutions of 9 wt. % Zonyl FSN-100 stirred at 375 rpm under Nitrogen flow rate of 1 L min$^{-1}$ using a thermostatted glass flow cell (S.A.=20 cm$^2$)
Figure 44:
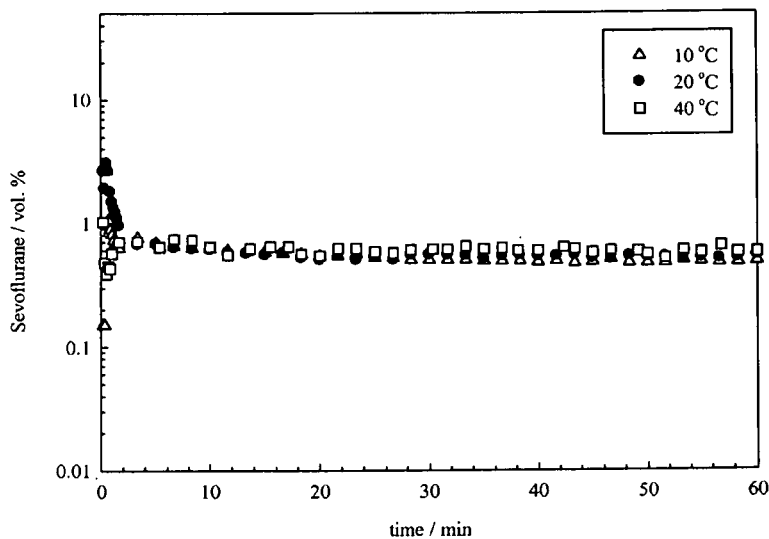
FIG. 44: Effect of temperature on Sevoflurane release profile of a formulation containing 15 mL Sevoflurane and 55 mL of an aqueous solution of 9 wt. % Zonyl FSN-100 stirred at different rates under Nitrogen flow rate of 1 L min$^{-1}$ using a thermostatted glass flow cell (S.A.=20 cm$^2$). The formulations were stirred at 400, 350 and 200 rpm at 10, 20 and 40° C., respectively.

The effect of temperature on anaesthetic release from formulations using Sevoflurane stabilised by Zonyl-FSN-100 surfactant is shown in FIG. 43. Increasing the temperature increases the release level of the Sevoflurane in the carrier gas, however, this can be compensated for by adjusting the stirring rate as shown in FIG. 44 where Sevoflurane release profiles using a fixed-composition formulation under Nitrogen flow rate of 1 L min$^{-1}$ at 10° C., 20° C. and 40° C. are stabilised at 1 MAC by stirring at 400, 350 and 200 rpm, respectively.

Effect of Surfactant Concentration on the Release Profile

Figure 45:
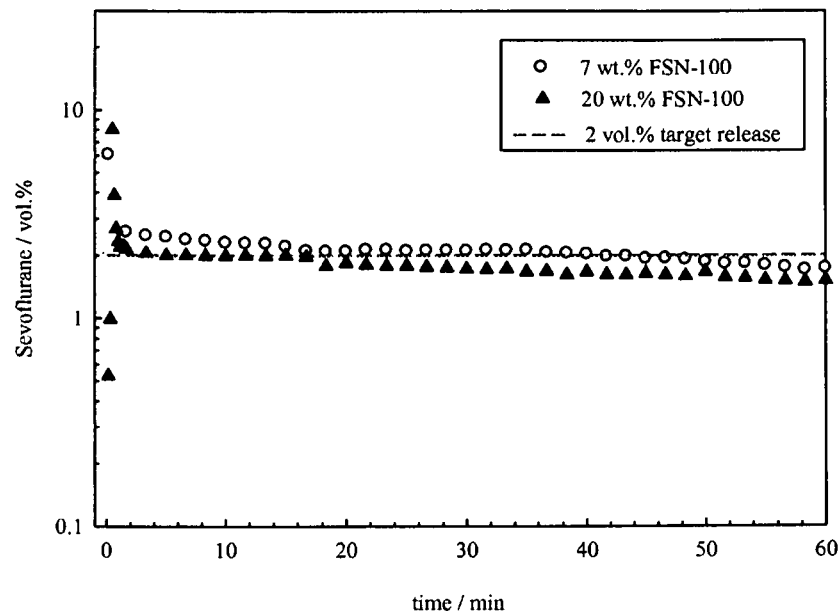
FIG. 45: Sevoflurane release profile of two formulations containing 15 mL Sevoflurane and 105 mL of aqueous solutions of 7 and 20 wt. % Zonyl FSN-100 under Nitrogen flow rate of 1 L min$^{-1}$ and stirring at 250 rpm using Flow-Rig Model 6 (S.A.=50 cm$^2$)

The effect of surfactant concentration, in this case Zonyl FSN-100, in the employed formulation on anaesthetic i.e. Sevoflurane release profile has been investigated. FIG. 45 shows Sevoflurane release profile of two formulations contain 15 mL Sevoflurane and Zonyl FSN-100 concentration of 7 and 20 wt. %. As shown in this figure, the formulation with lower surfactant concentration gives rise to a higher Sevoflurane release. For example, the concentration of the released Sevoflurane form the formulation with 7 wt. % FSN-100 at 30 minutes was 2.1 vol. % while the corresponding released concentration from the formulation with 20 wt. % FSN-100 was 1.72 vol. %.

Effect of Magnet Size on the Release Profile

Figure 46:
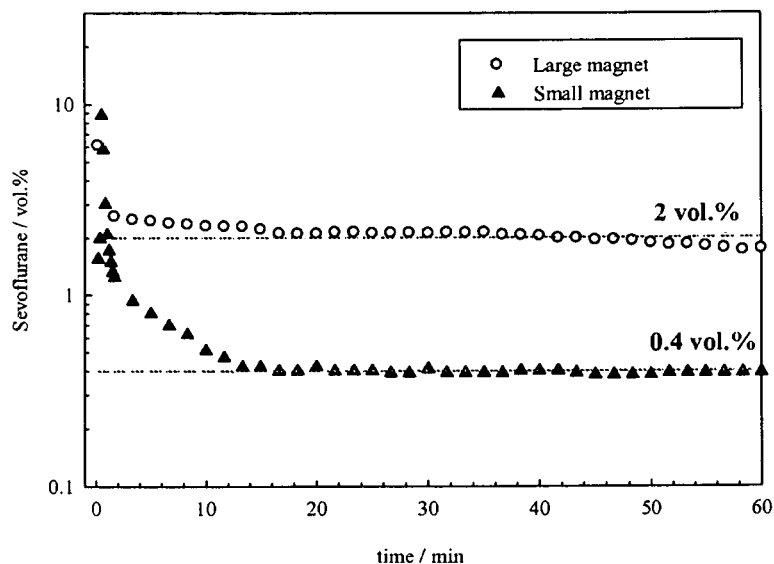
FIG. 46: Sevoflurane release profile of a formulation containing 15 mL Sevoflurane and 105 mL of aqueous solutions of 7 wt. % Zonyl FSN-100 under Nitrogen flow rate of 1 L min$^{-1}$ and stirred using small 50×7 mm and large 60×10 mm bar magnets at 250 rpm using Flow-Rig Model 6 (S.A.=50 cm$^2$)

Changing the size of the stirrer bar alters the shear forces and the degree of mixing/agitation, resulting in a different release level as illustrated in FIG. 46.

All-in-One Release Formulations

Using the technology developed herein it is possible to provide formulations able to deliver different anaesthetic release amounts/vol % or MAC values depending upon the shearing forces, or stirring/agitation rate, to which the formulation is exposed.

For example, a Sevoflurane formulation has been developed for use at 1 L/min carrier gas flow rate that can be made to deliver different anaesthetic release amounts/vol % or MAC values solely by changing the stirring rate; this provides for prolonged release of anaesthetic at any fixed level. In the examples shown the release levels are from 4MAC downwards.

Formulations of this kind could therefore be used to provide the highest concentration of anaesthetic required for induction of anaesthesia, followed by a sustained release at a lower concentration to maintain anaesthesia, whilst maintaining the flexibility to increase and decrease the delivered concentration by adjusting the stirring rate in a controlled manner.

Unless otherwise stated in the text, the data in these All-In-One Release Formulations were obtained at room temperature (20±2° C.) using flow rig model 6 (surface area 50 cm²), under a nitrogen flow rate of 1 L$^{-1}$.

An analogous formulation has been prepared for Isoflurane to, function at room temperature (20±2° C.) using flow rig model 6 (surface area 50 cm²), under a nitrogen flow rate of 1 L min$^{-1}$.

Two further formulations have been prepared which exemplify the same concept for use at a higher nitrogen flow rate of 4 L/min at room temperature (20±2° C.) using flow rig model 6 (surface area 50 cm²).

Sevoflurane at 1 L/Min

Figure 47:
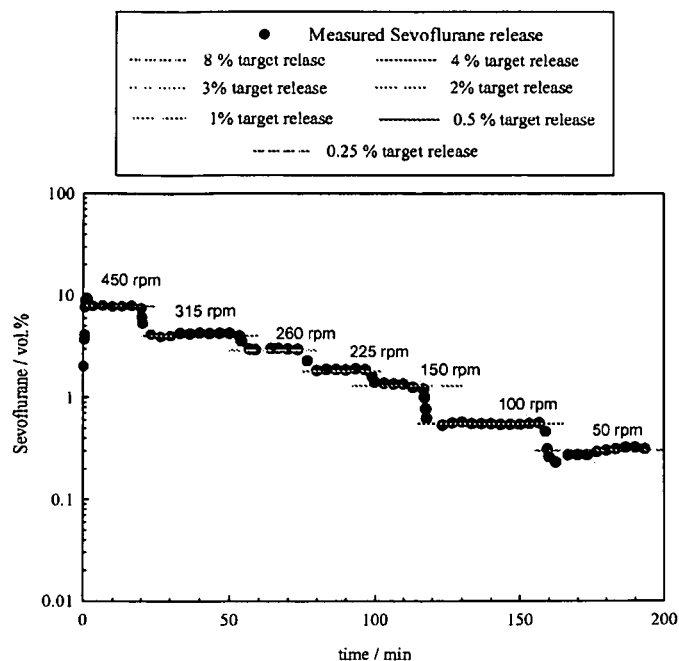
FIG. 47: Sevoflurane release profile of a formulation containing 50 mL sevoflurane and 110 mL of aqueous solutions of 15 wt. % Zonyl FSN-100 under Nitrogen flow rate of 1 L min$^{-1}$ as a function of stirring speed using Flow-Rig Model 6 (S.A.=50 cm$^2$)

FIG. 47 shows the release for a formulation containing 50 ml Sevoflurane dispersed by manual shaking in 110 ml of an aqueous solution of 15 wt % Zonyl FSN-100. The stirring rate has been adjusted to obtain different release levels at constant flow rate, as summarised in table 10.

The required induction level of 4MAC (anaesthetic release 8 vol %) has been maintained for 20 minutes to illustrate that the formulation could be used to rapidly induce and then maintain anaesthesia at the desired MAC/vol %. Any desired intermediate value between those explicitly demonstrated in FIG. 47 can be obtained by adjustment to the stirring of the system. As previously described, stirring rates are representative of the specific experimental set-up rather than absolute values; different stirring rates would be required using different apparatus or agitation methods, never the less, each individual cartridge can be calibrated to take this into account having regard to the shearing apparatus contained therein and/or method used. Notably, the principle concept i.e. to obtain controlled variation in release, of the amount of anaesthetic by changing the speed/manner of stirring holds across other stirring or agitation mechanisms. It should also be self-evident, based on the data herein that the timescales are indicative only of the experiment; the lower the release required the longer the fixed volume formulation will deliver a constant MAC. This is a general point that applies to all of the formulations where release is influenced by shearing/stirring rate.

All-in-One Isoflurane Release Formulation for 1 L/Min

Figure 48:
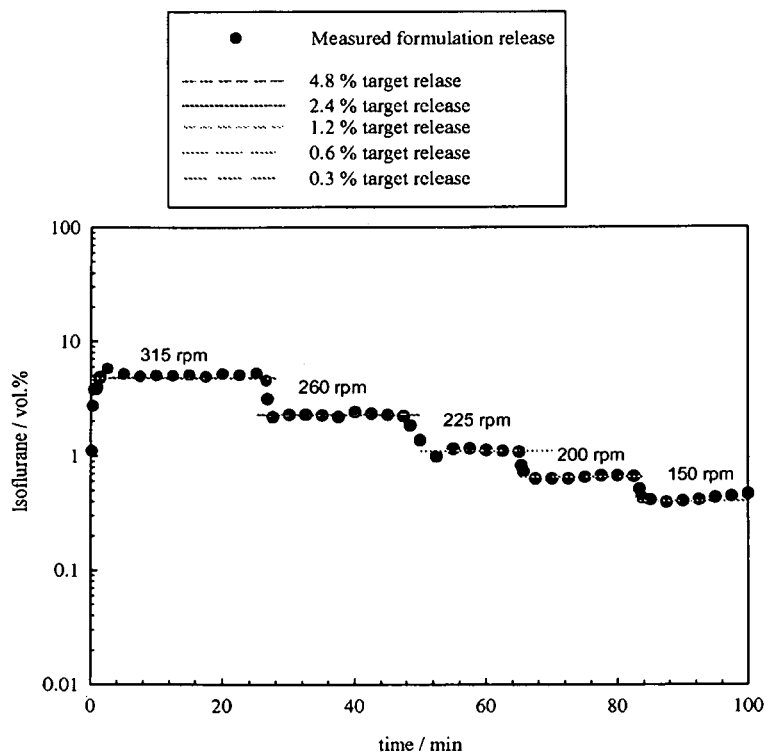
FIG. 48: Isoflurane release profile of a formulation containing 20 mL Isoflurane and 100 mL of aqueous solutions of 16 wt. % Zonyl FSN-100 under Nitrogen flow rate of 1 L min$^{-1}$ as function of stirring using Flow-Rig Model 6 (S.A.=50 cm$^2$)

FIG. 48 shows the release for a formulation containing 20 ml Sevoflurane dispersed by manual shaking in 100 ml of an aqueous solution of 16 wt % Zonyl FSN-100. The stirring rate has been adjusted to obtain different release levels at constant flow rate, as summarised in table 11.

All-in-One Release Formulations for 4 L/Min

Figure 49A:
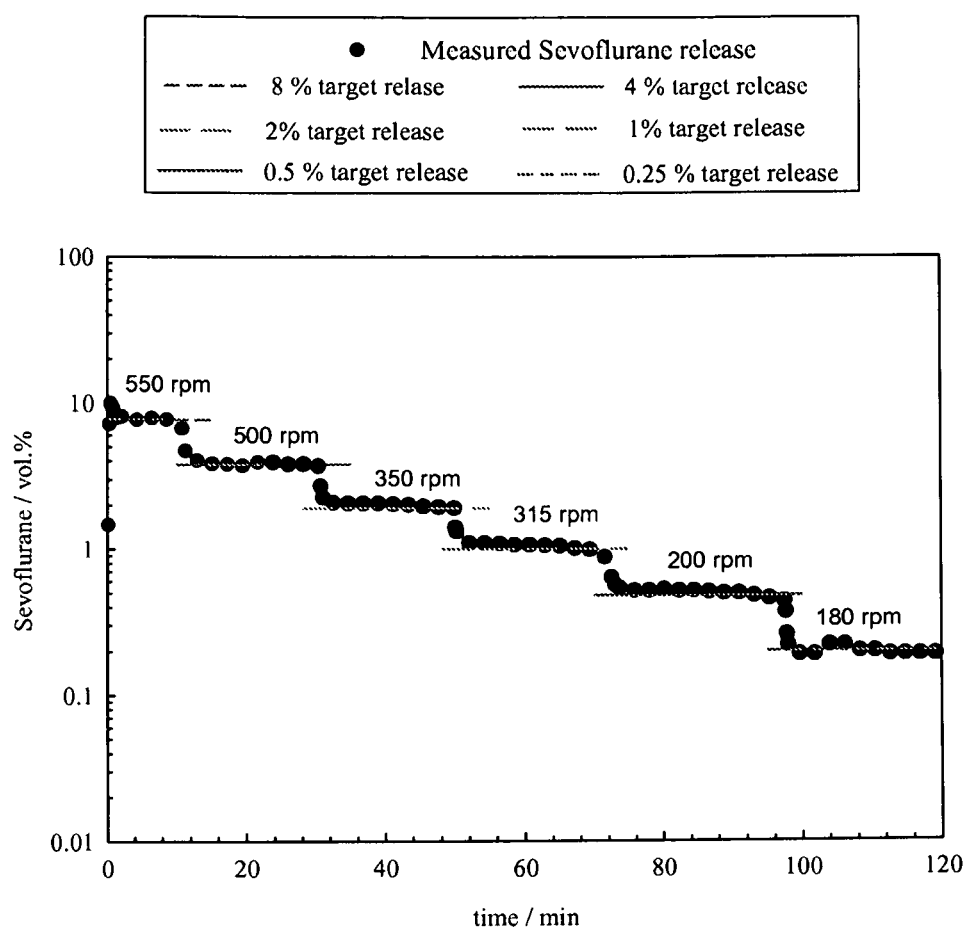
FIG. 49a: Sevoflurane release profile of a formulation containing 70 mL Sevoflurane and 90 mL of aqueous solutions of 20 wt. % Zonyl FSN-100 under Nitrogen flow rate of 4 L min$^{-1}$ as function of stirring using Flow-Rig Model 6 (S.A.=50 cm$^2$)

FIG. 49a shows the analogous release behaviour to that presented in FIG. 47, but at a higher carrier gas flow rate of 4 L/min. The stirring rate data is summarised in Table 12.

Figure 49B:
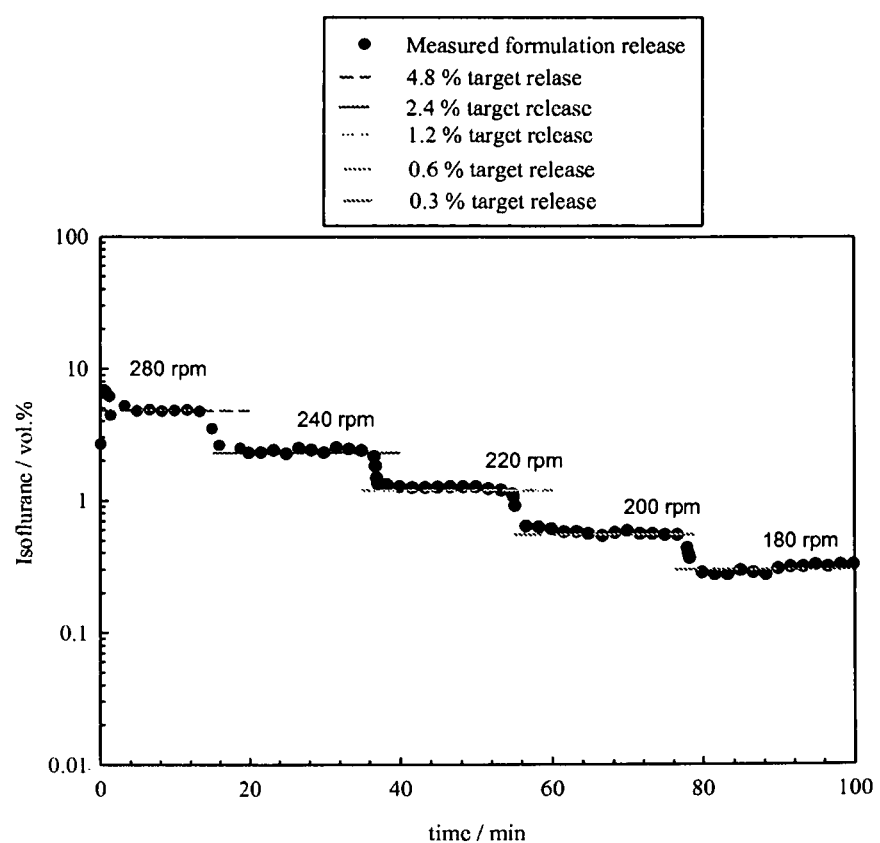
FIG. 49b: Isoflurane release profile of a formulation containing 50 mL Isoflurane and 70 mL of aqueous solution of 40 wt. % Zonyl FSN-100 under Nitrogen flow rate of 4 L min$^{-1}$ as function of stirring using Flow-Rig Model 6 (S.A.=50 cm$^2$)

FIG. 49b) shows the analogous release behaviour to that presented in FIG. 48, but at a higher carrier gas flow rate of 4 L/min. The stirring rate data is summarised in Table 13.

Emulsions Prepared Using Microemulsions

Figure 50:
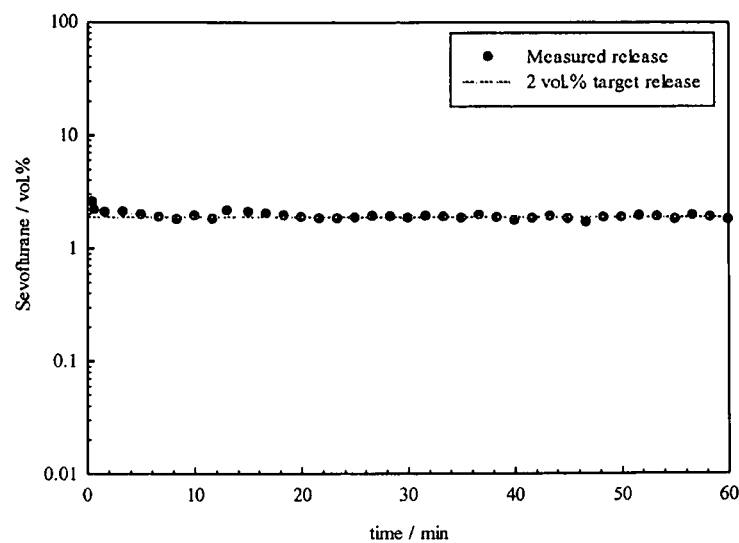
FIG. 50: Sevoflurane release profile of 65 mL formulation containing 10 mL Sevoflurane and 55 mL of aqueous solution of 30 wt. % Polyfox-159 under Nitrogen flow rate of 1 L/min and stirring at 200-500 rpm using Flow Rig Model 6 (S.A.=50 cm$^2$)
Figure 51:
FIG. 51: Appearance of Sevoflurane microemulsion-formulation (65 mL) containing 10 mL Sevoflurane and 55 mL of aqueous solution of 30 wt. % Polyfox-159.
Figure 52:
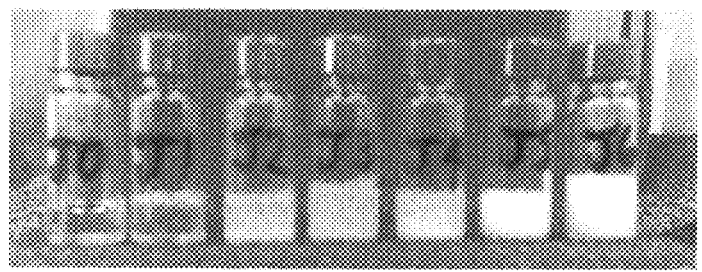
FIG. 52: Volatile fluorocarbon emulsion formed by shaking liquid HPFP in aqueous solution and surfactant solution, the increasingly hazy/opaque appearance of the liquid being indicative of emulsion formation.

FIG. 50 shows that the invention can be worked using a microemulsion. In the example given 10 mL Sevoflurane and 55 mL of aqueous solution of 30 wt. % Polyfox-159 produce a microemulsion that is optically transparent as shown in FIG. 51. The release profile of this microemulsuion shows the requisite controllable and constant rate for working the invention.

Emulsions Prepared from Pre-Gelled Anaesthetic

To illustrate the feasibility of storing the anaesthetic as a gel and then mixing with a surfactant solution to constitute the final formulation, samples of anaesthetic were pre-gelled using gelator G4, the structure for which is shown below. The gelator used (G4) contains two less CH2 groups in the hydrocarbon chain linking the two chiral centres.

Pre-gelation of the Sevoflurane was achieved by adding 0.15 g G4 to 1 ml Sevoflurane, heating to ca 70° C. and cooling in an ice bath. This heat-cool cycle was repeated twice to obtain a clear homogenous gel. On adding the required surfactant solution there is no mixing of the two phases but, on shaking, the sample appearance is the same as a control sample prepared from non-gelled anaesthetic, indicating that an emulsion is still formed. The samples were left to phase separate, and the liquid nature of the lower phase indicates that the gel is broken on mixing and the liquid anaesthetic is retained on phase separation.

CONCLUSION

The formulation of a volatile fluorocarbon liquid such as an anaesthetic as a stabilised dispersion greatly reduces the measured concentration of that fluorocarbon in a stream of carrier gas passed over the formulation when compared to the concentrations measured over the bare fluorocarbon liquid, or the same fluorocarbon liquid with a layer of water above it. Hence, forming a dispersion reduces the dangerously high levels of anaesthetic delivered in the carrier gas. Over time, all (>99%) of the volatile anaesthetic is released from the formulation, and the remaining surfactant solution can then be recharged with anaesthetic and re-used. Under constant gas flow rates, after a short initiation period when higher levels of anaesthetic are released the concentration remains constant until all the anaesthetic is released from the formulation. Hence the desired profile for anaesthetic delivery has been demonstrated. The levels of anaesthetic recorded are within safe and appropriate clinical limits, and are reproducible from sample to sample. Hence the formulation allows controlled, prolonged delivery of an anaesthetic over a predictable timescale.

The anaesthetic concentration in the carrier gas may be increased by flowing the carrier gas through the formulation, rather than through the head-space of the containment vessel. This also offers control of the concentration versus time release profile. Alternatively, the dispersion can be agitated to alter the rate of release of anaesthetic therefrom. Table 1 shows that the model anaesthetic molecule 2H,3H-perfluoropentane (HPFP) may be formulated to provide a high content of volatile fluorocarbon liquid by shaking the liquid with an aqueous in a surfactant solution. The hazy/opaque appearance of the samples is indicative of emulsion formation.

TABLE 1

Formulation fluorocarbon content as volume and weight percentage of the volatile fluorocarbon liquid in formulations containing the model anaesthetic fluorocarbon HPFP in a surfactant solution.

| sample | J0 | J1 | J2 | J3 | J4 | J5 | J6 | J7 |
|---|---|---|---|---|---|---|---|---|
| vol % HPFP | 0 | 5 | 9 | 13 | 17 | 29 | 38 | 50 |
| wt % HPFP | 0 | 1.5 | 3 | 4 | 5 | 9 | 11 | 15 |

Table 2 shows the moderation of evaporation by formulation of the model anaesthetic liquid HPFP.

TABLE 2

Release characteristics of the volatile fluorocarbon liquid 2H,3H perfluoropentane (HPFP) in different formulation conditions. 3 ml of HPFP was used either alone, under an equal volume of water or after mixing with a surfactant solution to provide a formulation containing 30 wt % HPFP. The HPFP was monitored using the sevoflurane setting on the anaesthetic monitor, hence the data is reported in units of sevoflurane % and represents a relative concentration only. Reported are the 'sevoflurane' concentrations recorded 30 seconds after mixing of the formulation and the time taken for the detected concentration to drop to zero.

| No $N_2$ flow | | J1 | J2 | J3 | J4 | J5 | J6 | J7 |
|---|---|---|---|---|---|---|---|---|
| Sevo % @ 30 s | HPFP only | | 1.9 | | 2.0 | | 2.8 | 2.9 |
| | emulsion | 0.04 | | | | 0.17 | | |
| time to 0% Sevo/s | HPFP | | 135 | | 140 | | 335 | 900 |
| | emulsion | 630 | | | | >1200* | | |

Table 3 shows how the moderation of evaporation by formulation of the model anaesthetic liquid HPFP can be further controlled by flowing the carrier gas over and especially through the sample in the testing chamber.

TABLE 3

Release characteristics of the volatile fluorocarbon liquid 2H,3H perfluoropentane (HPFP) in different formulation conditions. 3 ml of HPFP was used either alone, under an equal volume of water or after mixing with a surfactant solution to provide a formulation containing 30 wt % HPFP. 2 L min$^{-1}$ nitrogen carrier gas was flowed either over or through each sample. The HPFP was monitored using the sevoflurane setting on the anaesthetic monitor, hence the data is reported in units of scvoflurane % and represents a relative concentration only. Reported data are the sevoflurane concentrations recorded 30 seconds after mixing of the formulation and the time taken for the detected concentration to drop to zero.

| 21 min-1 $N_2$ | | HPFP | HPFP under water | 30% emulsion |
|---|---|---|---|---|
| Over | sevoflurane % @ 30 s | 1.6 | 0.62 | 0.04 |
| Through | sevoflurane % @ 30 s | — | — | 0.56 |
| Over | Time to 0% sevoflurane/s | 220 | 270 | >1500 |
| through | Time to 0% sevoflurane/s | <220 | 210 | 570 |

Table 4 shows how the concentration of volatile liquid in the carrier gas and the time taken to release all of the anaesthetic can be affected by the flow of carrier gas through the sample, and how the effects of formulation on retarding volatile release are maintained under these conditions.

TABLE 4

Release characteristics of the a volatile fluorocarbon liquid 2H,3H
perfluoropentane (HPFP) in different formulation conditions. 3 ml of HPFP
was used under an equal volume of water. Nitrogen carrier gas was flowed
through each sample at different flow rates. The HPFP was monitored using
the sevoflurane setting on the anaesthetic monitor, hence the data is reported
in units of sevoflurane % and represents a relative concentration only.
Reported data are the sevoflurane concentrations recorded 30 seconds after
mixing of the formulation and the time taken for the detected
concentration to drop to zero.

| 3 ml HPFP under 3 ml H$_2$O | | | J5 under same conditions | | |
|---|---|---|---|---|---|
| N2 flowrate through sample/ L min$^{-1}$ | % sevoflurane @ 30 s | time to 0% sevoflurane $^a$/ mins | N2 flowrate through sample | % sevoflurane @30 s | time to 0% sevoflurane/ mins |
| 0 L min$^{-1}$ | 1.5 | 8.5 | 0 L min$^{-1}$ | 0.04 | 20 |
| 1 L min$^{-1}$ | 2.5 | 4.5 | 1 L min$^{-1}$ | — | — |
| 2 L min$^{-1}$ | 2.3 | 3.5 | 2 L min$^{-1}$ | 0.56 | 10 |
| 3 L min$^{-1}$ | 2.2 | 3.0 | 3 L min$^{-1}$ | — | — |

$^a$ monitored as sevoflurane

TABLE 5

Zonyl FSN-100 stabilised emulsions. Tested in flow rig 6 (50 cm$^2$ surface area)

| | Release level/ vol % | MAC equiv-alent | Formulation Details | | | | Test Conditions | | | Character-isation Droplet size (Average)/nm | REF |
|---|---|---|---|---|---|---|---|---|---|---|---|
| | | | Total vol of formulation/ml | Vol Anaes-thetic/ ml | Vol % Anaes-thetic in formulation | Concentration of surfactant in aqueous stock solution/wt % | Carrier gas flow rate/L min$^{-1}$ | Temp/ ° C. | Stirring rate/rpm | | |
| SEVO-FLURANE | 4 | 2 | 160 | 50 | 31.2 | 18 | 1 | 20 | 312-375 | 209 (±2) | ZS4.01 |
| | 3.5 | 1.75 | 160 | 40 | 25.0 | 20 | 1 | 20 | 375 | 118 (±2) | ZS3.51 |
| | 3 | 1.5 | 134 | 26 | 19.4 | 10.0 | 1 | 20 | 300 | 259 (±0.6) | ZS3.01 |
| | 2 | 1 | 120 | 15 | 12.5 | 7.0 | 1 | 20 | 250 | 261 (±4) | ZS2.01 |
| | 1 | 0.5 | 120 | 7.5 | 6.3 | 4.0 | 1 | 20 | 250 | 239 (±5) | ZS1.01 |
| | 0.5 | 0.25 | 90 | 5.5 | 6.1 | 8 | 1 | 20 | 150 | 188 (±4) | ZS0.51 |
| ISO-FLURANE | 2.4 | 2 | 100 | 15 | 15 | 22 | 1 | 20 | 260-400 | 225 (±2) | ZI2.41 |
| | 1.8 | 1.5 | 120 | 18 | 15 | 25 | 1 | 20 | 400-500 | 340 (±7) | ZI1.81 |
| | 1.6 | 1.33 | 100 | 13 | 13 | 13 | 1 | 20 | 260 | 360 (±7) | ZI1.61 |
| | 1.2 | 1 | 100 | 9 | 9 | 11 | 1 | 20 | 200 | 430 (±8) | ZI1.21 |
| | 1.2 | 1 | 110 | 12 | 11 | 12 | 1 | 20 | 200 | 208 (±7) | ZI1.2b1 |
| | 0.6 | 0.5 | 100 | 4.5 | 4.5 | 8 | 1 | 20 | 200 | 200 (±6) | ZI0.61 |
| | 0.3 | 0.25 | 80 | 2.5 | 3.1 | 13 | 1 | 20 | 150 | 153 (±2) | ZI0.31 |

TABLE 6

Sevoflurane emulsions stabilised by other surfactants. Tested in flow rig 6 (50 cm$^2$ surface area)

| Surfactant | Release level/ vol % | MAC | Formulation Details | | | | Test Conditions | | | Character-isation Droplet size (Average)/nm | REF |
|---|---|---|---|---|---|---|---|---|---|---|---|
| | | | Total vol of formulation/ml | Vol Sevo-flurane/ ml | Vol % of Sevo-flurane in formulation | Concentration of surfactant in aqueous stock solution | Carrier gas flow rate/L min$^{-1}$ | Temp/ ° C. | Stirring rate/rpm | | |
| Capstone FS-3100 + Polyfox 159 | 2 | 1 | 130 | 15 | 11.5 | 3 wt % (C) + 10 wt % (P) | 1 | 20 | 250 | 142 (±2) | CPS2.01 |
| Capstone FS-3100 + Polyfox 159 | 2 | 1 | 130 | 18 | 13.8 | 9 wt % (C) + 5 wt % (P) | 1 | 20 | 230-250 | 245 (±5) | CPS2.0b1 |
| BrijO20 + Capstone FS-3100 | 2 | 1 | 130 | 20 | 15.3 | 10 wt %(B) + 12 wt % (C) | 1 | 20 | 250 | 318 (±3) | BCS2.01 |

TABLE 6-continued

Sevoflurane emulsions stabilised by other surfactants. Tested in flow rig 6 (50 cm² surface area)

| Surfactant | Release level/ vol % | MAC | Total vol of formulation/ml | Vol Sevoflurane/ml | Vol % of Sevoflurane in formulation | Concentration of surfactant in aqueous stock solution | Carrier gas flow rate/L min$^{-1}$ | Temp/ °C. | Stirring rate/rpm | Characterisation Droplet size (Average)/nm | REF |
|---|---|---|---|---|---|---|---|---|---|---|---|
| Polyfox 159 | 2 | 1 | 130 | 23 | 23.0 | 10 wt % P | 1 | 20 | 50-250 | 200 (±1) | PS2.01 |
| Capstone FS-3100 + Polyfox 159 | 1 | 0.5 | 130 | 15 | 11.5 | 5 wt % (C) + 3 wt % (P) | 1 | 20 | 230 | 346 (±8) | CPS1.01 |
| Brij O5 (B); Tween 20 (T) | 0.5 | 0.25 | 50 | 5 | 10 | 20 wt % B + 7 wt % T | 1 | 20 | 200 | 626 (±17) | BTS0.5 |

Abbreviations: Capstone FS-3100 (C); Polyfox 159 (P); Brij O20 (B)

TABLE 7

Effect of stirring rate on release. Tested using formulation ZS2.0 at constant temperature and flow rate in flow rig 6 (50 cm² surface area)

| | | Total vol of formulation/ml | Vol Sevoflurane/ml | Vol % Sevoflurane in formulation | Concentration of surfactant in aqueous stock solution/wt % | Carrier gas flow rate/L min$^{-1}$ | Temp/ °C. | Stirring rate/rpm | Release level/ vol % | MAC equivalent |
|---|---|---|---|---|---|---|---|---|---|---|
| SEVOFLURANE | ZS2.01 | 120 | 15 | 12.5 | 7.0 | 1 | 20 | 100 | 0.7 | 0.35 |
| | | | | | | 1 | 20 | 150 | 1.3(ave) | 0.65 |
| | | | | | | 1 | 20 | 200 | 1.4(ave) | 0.7 |
| | | | | | | 1 | 20 | 250 | 2.0 | 1 |
| | | | | | | 1 | 20 | 315 | 3.0 | 1.5 |
| | | | | | | 1 | 20 | 500 | 3.4(ave) | 1.7 |

TABLE 8

Release at 4 L min$^{-1}$ flow rate. Zonyl FSN-100 stabilised emulsions tested in flow rig 6 (50 cm² surface area). Flow rate = 4 L min$^{-1}$

| | Release level/ vol % | MAC equivalent | Total vol of formulation/ml | Vol Anaesthetic/ml | Concentration of anaesthetic in formulation/ vol % | Concentration of surfactant in aqueous stock solution/wt % | Carrier gas flow rate/L min$^{-1}$ | Temp/ °C. | Stirring rate/rpm | Characterisation Droplet size (Average)/nm | REF |
|---|---|---|---|---|---|---|---|---|---|---|---|
| SEVOFLURANE | 4 | 2.0 | 160 | 70 | 43.8 | 25 | 4 | 20 | 500-1000 | 256 (±5) | ZS4.04 |
| | 3 | 1.5 | 140 | 50 | 35.7 | 22 | 4 | 20 | 375-625 | 206 (±2) | ZS3.04 |
| | 2 | 1.0 | 140 | 40 | 28.6 | 17 | 4 | 20 | 375-625 | 384 (±5) | ZS2.04 |
| | 0.5 | 0.25 | 120 | 15 | 12.5 | 7 | 4 | 20 | 250 | 188 (±4) | ZS0.54 = ZS2.01 |
| ISOFLURANE | 2.4 | 2.0 | 140 | 35 | 0.25 | 19 | 4 | 20 | 375-1000 | 884 (±5) | ZI2.44 |

TABLE 9

Emulsions stabilised by other surfactants tested in flow rig 6 (50 cm² surface area). Flow rate = 4 L min$^{-1}$

| | Release level/ vol % | MAC equivalent | Total vol of formulation/ml | Vol Sevoflurane/ml | Concentration of anaesthetic in formulation/ vol % | Concentration of surfactant in aqueous stock solution/wt % | Carrier gas flow rate/L min$^{-1}$ | Temp/ °C. | Stirring rate/rpm | Characterisation Droplet size (Average)/nm | REF |
|---|---|---|---|---|---|---|---|---|---|---|---|
| ISOFLURANE | 2.4 | 2.0 | 130 | 30 | 23.0 | 5S + 6C | 4 | 20 | 300-750 | 480 (±5) | GCI2.44 |

Abbreviations: Capstone FS-3100 (C); Chemguard S-550L-100 (S)

TABLE 10

Summary stirring rates used to generate release profile data presented in FIG. 47.

| Sevoflurane level/vol | MAC | duration | Stirring rate |
|---|---|---|---|
| 8 (±0.2) | 4 | 20 | 400-500 |
| 4 (±0.2) | 2 | 30 | 315-400 |
| 3 (±0.2) | 1.5 | 20 | 260-315 |
| 2 (±0.2) | 1 | 20 | 225-250 |
| 1 (±0.2) | 0.5 | 15 | 150 |
| 0.5 (±0.1) | 0.25 | 40 | 100 |
| 0.25 (±0.1) | 0.125 | 30 | 50 |

TABLE 11

Summary stirring rates used to generate release profile data presented in FIG. 48.

| Isoflurane level/vol | MAC | duration | Stirring rate |
|---|---|---|---|
| 4.8 (±0.2) | 4 | 20 | 315-375 |
| 2.4 (±0.2) | 2 | 15 | 260-315 |
| 1.2 (±0.1) | 1 | 15 | 225-250 |
| 0.6 (±0.1) | 0.5 | 20 | 200 |
| 0.3 (±0.1) | 0.25 | 20 | 150 |

TABLE 12

Summary stirring rates used to generate release profile data presented in FIG. 49a.

| Sevoflurane level/vol % | MAC | duration/min | Stirring rate/rpm |
|---|---|---|---|
| 8 (±0.2) | 4 | 20 | 550-750 |
| 4 (±0.2) | 2 | 30 | 500-650 |
| 2 (±0.2) | 1 | 20 | 350 |
| 1 (±0.2) | 0.5 | 15 | 315 |
| 0.5 (±0.1) | 0.25 | 40 | 200 |
| 0.25 (±0.1) | 0.125 | 30 | 180 |

TABLE 13

Summary of stirring rates used to generate release profile data presented in FIG. 49 b.

| Isoflurane level/vol % | MAC equivalent | duration/min | Stirring rate/rpm | REF |
|---|---|---|---|---|
| 4.8 (±0.2) | 4 | 15 | 280-400 | AIO_1_4 |
| 2.4 (±0.2) | 2 | 15 | 240-300 | |
| 1.2 (±0.1) | 1 | 15 | 220-250 | |
| 0.6 (±0.05) | 0.5 | 20 | 200-250 | |
| 0.3 (±0.05) | 0.25 | 20 | 180-225 | |

The invention claimed is:

1. An anaesthetic cartridge for use with an inhalation device for human or veterinary use to deliver an inhalational or volatilised anaesthetic to a patient, wherein said anaesthetic cartridge comprises:
   an adjustable stirrer or agitator;
   a non-volatile anaesthetic control release medium provided as an emulsion; and
   at least one selected inhalational or volatilised anaesthetic;
   wherein an amount of said non-volatile anaesthetic control release medium relative to said at least one selected inhalational or volatilised anaesthetic is such that when using said adjustable stirrer or agitator only the selected at least one inhalational or volatilised anaesthetic is delivered at a selected Minimum alveolar concentration (MAC), at a substantially constant or controllable rate, within the range of 0.25-4.0× Minimum alveolar concentration (MAC) thereby allowing for either i) induction and/or maintenance of anaesthesia or ii) sedation.

2. The anaesthetic cartridge according to claim 1 wherein said at least one selected inhalational or volatilised anaesthetic is dispersed or distributed in said non-volatile anaesthetic control release medium in a stable and chemically unaltered state.

3. The anaesthetic cartridge according to claim 1 wherein said emulsion is provided by one or more non-ionic surfactants selected from the group consisting of halogenated non-ionic surfactants, ethylene oxide based fluorocarbon surfactants, propylene oxide or ethylene oxide based hydrocarbon surfactants, partially fluorinated sulfosuccinate surfactants and branched hydrocarbon sulfosuccinate surfactants.

4. The anaesthetic cartridge according to claim 1 wherein said emulsion has a droplet size between 10-1000 nm.

5. The anaesthetic cartridge according to claim 1 wherein an anaesthetic content is between 0.25-44% by volume.

6. The anaesthetic cartridge according to claim 1 wherein said anaesthetic cartridge further comprises a gelling agent.

7. The anaesthetic cartridge according to claim 6 wherein the gelling agent comprises chiral, non-racemic bis-($\alpha,\beta$-dihydroxy ester)s.

8. The anaesthetic cartridge according to claim 1 wherein said non-volatile anaesthetic control release medium and said at least one selected inhalational or volatilised anaesthetic when mixed together in said anaesthetic cartridge have a surface area within the anaesthetic cartridge that is between 10-60 cm$^2$.

9. The anaesthetic cartridge according to claim 8 wherein said surface area is 50 cm$^2$.

10. The anaesthetic cartridge according to claim 1 wherein said at least one selected inhalational or volatilised anaesthetic is selected from one or more of the group consisting of: desflurane, isoflurane, halothane, enflurane, sevoflurane, and methoxyflurane.

11. The anaesthetic cartridge according to claim 1 wherein the anaesthetic cartridge works over a temperature range of 4° C. to 40° C.

12. The anaesthetic cartridge according to claim 11 wherein said anaesthetic cartridge works at a temperature of 20° C.

13. An inhalation device for human or veterinary use comprising:
   a mask for positioning over the face of a patient;
   a supply of breathable gas in fluid communication with said mask; and
   at least one anaesthetic cartridge according to claim 1;
   wherein said inhalation device is adapted or configured such that an anaesthetic released from said anaesthetic cartridge is mixed with said breathable gas before being delivered to said patient.

* * * * *